(12) United States Patent
Donohoe et al.

(10) Patent No.: US 8,012,164 B1
(45) Date of Patent: Sep. 6, 2011

(54) METHOD AND APPARATUS FOR CREATING AN OPENING IN THE WALL OF A TUBULAR VESSEL

(75) Inventors: Brendan M. Donohoe, San Francisco, CA (US); Theodore M. Bender, San Francisco, CA (US); Brian R. DuBois, Redwood City, CA (US); Scott O. Chamness, Menlo Park, CA (US); Stephen A. Yencho, Menlo Park, CA (US); Jaime S. Vargas, Menlo Park, CA (US); Nathan H. White, Palo Alto, CA (US); Gregory B. Arcenio, Redwood City, CA (US); Heather L. Klaubert, Decatur, GA (US); Russell C. Mead, Jr., Mountain View, CA (US)

(73) Assignee: Cardica, Inc., Redwood City, CA (US)

( * ) Notice: Subject to any disclaimer, the term of this patent is extended or adjusted under 35 U.S.C. 154(b) by 2498 days.

(21) Appl. No.: 10/054,745

(22) Filed: Jan. 22, 2002

(51) Int. Cl.
*A61B 17/04* (2006.01)
*A61B 17/14* (2006.01)
(52) U.S. Cl. ........ 606/167; 606/153; 606/154; 606/155; 606/169; 606/170; 606/171; 606/180; 606/181
(58) Field of Classification Search .................. 606/170, 606/180, 184, 185, 159, 167, 171, 153, 154, 606/155, 181; 600/566, 567
See application file for complete search history.

(56) References Cited

U.S. PATENT DOCUMENTS

| 3,254,650 | A |   | 6/1966  | Collito          |        |
|-----------|---|---|---------|------------------|--------|
| 3,519,187 | A |   | 7/1970  | Kapitanov et al. |        |
| 3,577,979 | A |   | 5/1971  | van der Gaast    |        |
| 3,774,615 | A |   | 11/1973 | Lim et al.       |        |
| 3,825,362 | A | * | 7/1974  | Hougen           | 408/68 |
| 4,018,228 | A |   | 4/1977  | Goosen           |        |
| 4,076,162 | A |   | 2/1978  | Kapitanov et al. |        |
| 4,118,806 | A |   | 10/1978 | Porier et al.    |        |
| 4,214,587 | A |   | 7/1980  | Sakura, Jr.      |        |
| 4,216,776 | A |   | 8/1980  | Downie et al.    |        |
| 4,217,664 | A |   | 8/1980  | Faso             |        |

(Continued)

FOREIGN PATENT DOCUMENTS
WO    WO-00/76405    12/2000

OTHER PUBLICATIONS

"Cardica PAS-Port Proximal Anastomosis System 510(k)", Section VI.C., "Substantial Equivalence", and Attachment 7 (Unpublished).

(Continued)

*Primary Examiner* — Vy Q Bui
(74) *Attorney, Agent, or Firm* — Brian A. Schar

(57) ABSTRACT

An auger is axially fixed to and positioned within a cutter. The auger and cutter advance at the same time relative to a contact structure placed against a vessel, penetrating the wall of the vessel and cutting a tissue plug. When the auger and the cutter are retracted from the vessel wall, the tissue plug is retained by the auger and cutter and removed from the vessel wall. The auger and the cutter thus create an opening in the vessel wall, without the need for a prior incision in that wall.

51 Claims, 11 Drawing Sheets

U.S. PATENT DOCUMENTS

| | | |
|---|---|---|
| 4,350,160 A | 9/1982 | Kolesov et al. |
| 4,352,358 A | 10/1982 | Angelchik |
| 4,366,819 A | 1/1983 | Kaster |
| 4,368,736 A | 1/1983 | Kaster |
| 4,503,568 A | 3/1985 | Madras |
| 4,523,592 A | 6/1985 | Daniel |
| 4,534,761 A | 8/1985 | Raible |
| 4,553,542 A | 11/1985 | Schenck et al. |
| 4,589,416 A | 5/1986 | Green |
| 4,593,693 A | 6/1986 | Schenck |
| 4,603,693 A | 8/1986 | Conta et al. |
| 4,607,637 A | 8/1986 | Berggren et al. |
| 4,624,255 A | 11/1986 | Schenck et al. |
| 4,624,257 A | 11/1986 | Berggren et al. |
| 4,657,019 A | 4/1987 | Walsh et al. |
| 4,665,906 A | 5/1987 | Jervis |
| 4,721,109 A | 1/1988 | Healey |
| 4,747,407 A | 5/1988 | Liu et al. |
| 4,752,024 A | 6/1988 | Green et al. |
| 4,873,991 A | 10/1989 | Skinner |
| 4,883,453 A | 11/1989 | Berry et al. |
| 4,907,591 A | 3/1990 | Vasconcellos et al. |
| 4,917,087 A | 4/1990 | Walsh et al. |
| 4,917,090 A | 4/1990 | Berggren et al. |
| 4,917,091 A | 4/1990 | Berggren et al. |
| 4,930,674 A | 6/1990 | Barak |
| 5,005,749 A | 4/1991 | Aranyi |
| 5,062,842 A | 11/1991 | Tiffany |
| 5,104,025 A | 4/1992 | Main et al. |
| 5,119,983 A | 6/1992 | Green et al. |
| 5,129,913 A | 7/1992 | Ruppert |
| 5,156,613 A | 10/1992 | Sawyer |
| 5,171,262 A | 12/1992 | MacGregor |
| 5,178,634 A | 1/1993 | Martinez |
| 5,187,796 A | 2/1993 | Wang et al. |
| 5,192,289 A | 3/1993 | Jessen |
| 5,192,294 A | 3/1993 | Blake, III |
| 5,193,731 A | 3/1993 | Aranyi |
| 5,205,459 A | 4/1993 | Brinkerhoff et al. |
| 5,217,474 A | 6/1993 | Zacca et al. |
| 5,221,281 A | 6/1993 | Klicek |
| 5,222,963 A | 6/1993 | Brinkerhoff et al. |
| 5,234,447 A | 8/1993 | Kaster et al. |
| 5,250,058 A | 10/1993 | Miller et al. |
| 5,250,060 A | 10/1993 | Carbo et al. |
| 5,271,544 A | 12/1993 | Fox et al. |
| 5,275,322 A | 1/1994 | Brinkerhoff et al. |
| 5,285,945 A | 2/1994 | Brinkerhoff et al. |
| 5,290,298 A | 3/1994 | Rebuffat et al. |
| 5,292,053 A | 3/1994 | Bilotti et al. |
| 5,304,220 A | 4/1994 | Maginot |
| 5,314,435 A | 5/1994 | Green et al. |
| 5,314,468 A | 5/1994 | Martinez |
| 5,324,300 A | 6/1994 | Elias et al. |
| 5,333,773 A | 8/1994 | Main et al. |
| 5,336,233 A | 8/1994 | Chen |
| 5,344,059 A | 9/1994 | Green et al. |
| 5,350,104 A | 9/1994 | Main et al. |
| 5,354,302 A | 10/1994 | Ko |
| 5,364,389 A | 11/1994 | Anderson |
| 5,366,462 A | 11/1994 | Kaster et al. |
| 5,392,979 A | 2/1995 | Green et al. |
| 5,395,030 A | 3/1995 | Kuramoto et al. |
| 5,395,311 A | 3/1995 | Andrews |
| 5,403,338 A | 4/1995 | Milo |
| 5,423,330 A | 6/1995 | Lee |
| 5,423,796 A * | 6/1995 | Shikhman et al. ................. 606/1 |
| 5,423,846 A * | 6/1995 | Fischell ........................ 606/180 |
| 5,443,497 A | 8/1995 | Venbrux |
| 5,447,514 A | 9/1995 | Gerry et al. |
| 5,454,825 A | 10/1995 | Van Leeuwen |
| 5,456,712 A | 10/1995 | Maginot |
| 5,456,714 A | 10/1995 | Owen |
| 5,462,062 A | 10/1995 | Rubinstein et al. |
| 5,464,449 A | 11/1995 | Ryan et al. |
| 5,465,895 A | 11/1995 | Knodel et al. |
| 5,470,320 A | 11/1995 | Tiefenbrun et al. |
| 5,478,354 A | 12/1995 | Tovey et al. |
| 5,488,958 A | 2/1996 | Topel et al. |
| 5,503,635 A | 4/1996 | Sauer et al. |
| 5,515,478 A | 5/1996 | Wang |
| 5,522,834 A | 6/1996 | Fonger et al. |
| 5,524,180 A | 6/1996 | Wang et al. |
| D372,310 S | 7/1996 | Hartnett |
| 5,533,661 A | 7/1996 | Main et al. |
| 5,540,677 A | 7/1996 | Sinofsky |
| 5,553,198 A | 9/1996 | Wang et al. |
| 5,556,405 A | 9/1996 | Lary |
| 5,558,667 A | 9/1996 | Yarborough et al. |
| 5,571,167 A | 11/1996 | Maginot |
| 5,591,187 A * | 1/1997 | Dekel ........................... 606/180 |
| 5,643,340 A | 7/1997 | Nunokawa |
| 5,645,520 A | 7/1997 | Nakamura et al. |
| 5,657,429 A | 8/1997 | Wang et al. |
| 5,669,918 A | 9/1997 | Balazs et al. |
| 5,669,934 A | 9/1997 | Sawyer |
| 5,676,670 A | 10/1997 | Kim |
| 5,690,662 A | 11/1997 | Chiu et al. |
| 5,693,088 A | 12/1997 | Lazarus |
| 5,695,504 A | 12/1997 | Gifford, III et al. |
| 5,702,412 A | 12/1997 | Popov et al. |
| 5,707,362 A | 1/1998 | Yoon |
| 5,707,380 A | 1/1998 | Hinchliffe et al. |
| 5,709,335 A | 1/1998 | Heck |
| 5,709,693 A | 1/1998 | Taylor |
| 5,725,544 A | 3/1998 | Rygaard |
| 5,725,553 A | 3/1998 | Moenning |
| 5,732,872 A | 3/1998 | Bolduc et al. |
| 5,754,741 A | 5/1998 | Wang et al. |
| 5,755,778 A | 5/1998 | Kleshinski |
| 5,762,458 A | 6/1998 | Wang et al. |
| 5,779,718 A | 7/1998 | Green et al. |
| 5,782,853 A | 7/1998 | Zeevi et al. |
| 5,792,135 A | 8/1998 | Madhani et al. |
| 5,797,900 A | 8/1998 | Madhani et al. |
| 5,797,920 A | 8/1998 | Kim |
| 5,797,933 A | 8/1998 | Snow et al. |
| 5,799,661 A | 9/1998 | Boyd et al. |
| 5,799,857 A | 9/1998 | Robertson et al. |
| 5,807,377 A | 9/1998 | Madhani et al. |
| 5,814,073 A | 9/1998 | Bonutti |
| 5,815,640 A | 9/1998 | Wang et al. |
| 5,817,113 A | 10/1998 | Gifford, III et al. |
| 5,825,982 A | 10/1998 | Wright et al. |
| 5,827,316 A | 10/1998 | Young et al. |
| 5,833,698 A | 11/1998 | Hinchliffe et al. |
| 5,841,950 A | 11/1998 | Wang et al. |
| 5,855,583 A | 1/1999 | Wang et al. |
| 5,868,763 A | 2/1999 | Spence et al. |
| 5,868,764 A | 2/1999 | Rosengart |
| 5,871,495 A | 2/1999 | Mueller |
| 5,875,782 A | 3/1999 | Ferrari et al. |
| 5,878,193 A | 3/1999 | Wang et al. |
| 5,879,371 A | 3/1999 | Gardiner et al. |
| 5,881,943 A | 3/1999 | Heck et al. |
| 5,888,247 A | 3/1999 | Benetti |
| 5,893,369 A | 4/1999 | LeMole |
| 5,895,403 A | 4/1999 | Collinsworth |
| 5,895,404 A | 4/1999 | Ruiz |
| 5,904,697 A | 5/1999 | Gifford, III et al. |
| 5,907,664 A | 5/1999 | Wang et al. |
| 5,910,121 A | 6/1999 | Paolo et al. |
| 5,910,153 A | 6/1999 | Mayenberger |
| 5,911,036 A | 6/1999 | Wright et al. |
| 5,915,616 A | 6/1999 | Viola et al. |
| 5,921,995 A | 7/1999 | Kleshinski |
| 5,944,730 A | 8/1999 | Nobles et al. |
| 5,947,363 A | 9/1999 | Bolduc et al. |
| 5,957,363 A | 9/1999 | Heck |
| 5,968,089 A | 10/1999 | Krajicek |
| 5,976,159 A | 11/1999 | Bolduc et al. |
| 5,976,178 A | 11/1999 | Goldsteen et al. |
| 5,989,276 A | 11/1999 | Houser et al. |
| 5,989,278 A | 11/1999 | Mueller |
| 6,001,124 A | 12/1999 | Bachinski |
| 6,004,909 A | 12/1999 | Lindman |
| 6,007,544 A | 12/1999 | Kim |

| | | | |
|---|---|---|---|
| 6,013,190 A | 1/2000 | Berg et al. | |
| 6,015,416 A | 1/2000 | Stefanchik et al. | |
| 6,022,367 A | 2/2000 | Sherts | |
| 6,024,748 A | 2/2000 | Manzo et al. | |
| 6,025,015 A | 2/2000 | Landry-Coltrain et al. | |
| 6,030,370 A | 2/2000 | Kupka et al. | |
| 6,030,395 A | 2/2000 | Nash et al. | |
| 6,036,699 A | 3/2000 | Andreas et al. | |
| 6,036,700 A | 3/2000 | Stefanchik et al. | |
| 6,036,702 A | 3/2000 | Bachinski et al. | |
| 6,036,703 A | 3/2000 | Evans et al. | |
| 6,036,704 A | 3/2000 | Yoon | |
| 6,036,705 A | 3/2000 | Nash et al. | |
| 6,036,710 A | 3/2000 | McGarry et al. | |
| 6,050,472 A | 4/2000 | Shibata | |
| 6,053,390 A | 4/2000 | Green et al. | |
| 6,056,762 A | 5/2000 | Nash et al. | |
| 6,066,144 A | 5/2000 | Wolf et al. | |
| 6,066,148 A | 5/2000 | Rygaard | |
| 6,068,637 A | 5/2000 | Popov et al. | |
| 6,074,416 A | 6/2000 | Berg et al. | |
| 6,080,167 A | 6/2000 | Lyell | |
| 6,080,173 A * | 6/2000 | Williamson et al. | 606/184 |
| 6,080,175 A | 6/2000 | Hogendijk | |
| 6,080,176 A | 6/2000 | Young | |
| 6,083,234 A | 7/2000 | Nicholas et al. | |
| 6,083,238 A | 7/2000 | Alexander, Jr. et al. | |
| 6,110,188 A | 8/2000 | Narciso, Jr. | |
| 6,113,612 A | 9/2000 | Swanson et al. | |
| 6,117,148 A | 9/2000 | Ravo et al. | |
| 6,120,432 A | 9/2000 | Sullivan et al. | |
| 6,146,393 A | 11/2000 | Wakabayashi | |
| 6,149,681 A | 11/2000 | Houser et al. | |
| 6,152,937 A | 11/2000 | Peterson et al. | |
| 6,152,945 A | 11/2000 | Bachinski et al. | |
| 6,165,185 A | 12/2000 | Shennib et al. | |
| 6,167,889 B1 | 1/2001 | Benetti | |
| 6,171,319 B1 | 1/2001 | Nobles et al. | |
| 6,171,321 B1 | 1/2001 | Gifford, III et al. | |
| 6,176,413 B1 | 1/2001 | Heck et al. | |
| 6,176,864 B1 | 1/2001 | Chapman | |
| 6,176,867 B1 | 1/2001 | Wright | |
| 6,183,486 B1 | 2/2001 | Snow et al. | |
| 6,186,942 B1 | 2/2001 | Sullivan et al. | |
| 6,187,019 B1 | 2/2001 | Stefanchik et al. | |
| 6,187,020 B1 | 2/2001 | Zegdi et al. | |
| 6,190,392 B1 * | 2/2001 | Vandewalle et al. | 606/99 |
| 6,190,396 B1 | 2/2001 | Whitin et al. | |
| 6,190,397 B1 | 2/2001 | Spence et al. | |
| 6,190,590 B1 | 2/2001 | Randall et al. | |
| 6,193,129 B1 | 2/2001 | Bittner et al. | |
| 6,193,734 B1 | 2/2001 | Bolduc et al. | |
| 6,206,912 B1 | 3/2001 | Goldsteen et al. | |
| 6,206,913 B1 | 3/2001 | Yencho et al. | |
| 6,235,054 B1 | 5/2001 | Berg et al. | |
| 6,241,742 B1 | 6/2001 | Spence et al. | |
| 6,248,117 B1 | 6/2001 | Blatter | |
| 6,253,768 B1 | 7/2001 | Wilk | |
| 6,276,528 B1 | 8/2001 | Nowotny et al. | |
| 6,293,955 B1 | 9/2001 | Houser et al. | |
| 6,375,396 B1 * | 4/2002 | Fangmann et al. | 408/206 |
| 6,419,681 B1 | 7/2002 | Vargas et al. | |
| 6,485,496 B1 | 11/2002 | Suyker et al. | |
| 6,488,693 B2 * | 12/2002 | Gannoe et al. | 606/167 |
| 6,673,088 B1 * | 1/2004 | Vargas et al. | 606/185 |
| 6,685,630 B2 * | 2/2004 | Sauer et al. | 600/114 |
| 6,689,147 B1 * | 2/2004 | Koster, Jr. | 606/184 |
| 6,966,917 B1 | 11/2005 | Suyker et al. | |
| 2001/0000903 A1 | 5/2001 | Heck et al. | |
| 2001/0001122 A1 | 5/2001 | Gifford, III et al. | |
| 2001/0001124 A1 | 5/2001 | Mueller | |
| 2001/0004697 A1 | 6/2001 | Blatter et al. | |
| 2001/0004698 A1 | 6/2001 | Blatter et al. | |
| 2001/0016752 A1 | 8/2001 | Berg et al. | |
| 2001/0023354 A1 | 9/2001 | Blatter et al. | |
| 2001/0029384 A1 | 10/2001 | Nicholas et al. | |
| 2001/0037139 A1 | 11/2001 | Yencho et al. | |
| 2001/0047179 A1 | 11/2001 | Gifford, III et al. | |
| 2003/0065342 A1 | 4/2003 | Nobis | |

OTHER PUBLICATIONS

"Sales training brochure entitled "CorLink Automated Anastomosis Device"", (2002).

* cited by examiner

METHOD AND APPARATUS FOR CREATING AN OPENING IN THE WALL OF A TUBULAR VESSEL

FIELD OF THE INVENTION

The present invention relates generally to surgery, and more particularly to creating an opening in the wall of a tubular structure such as a blood vessel.

BACKGROUND

Anastomosis is a procedure where two separate tubular or hollow organs are surgically grafted together to form an intercommunication between them. Vascular anastomosis involves creating an anastomosis between blood vessels to create or restore blood flow. The vascular anastomosis procedure is routinely performed during the treatment of a variety of conditions, including coronary artery disease (CAD), neurovascular disease, diseases of the great and peripheral vessels, organ transplantation, and traumatic injury. When a patient suffers from CAD, an occlusion or stenosis in a coronary artery restricts blood flow to the heart muscle. To treat CAD, the area where the occlusion occurs is bypassed to reroute blood flow by placing a graft vessel (in the form of a harvested artery or vein, prosthesis, allograft or xenograft) between two target vessels: the aorta or other supply of arterial blood, and the coronary artery. Placement of the graft vessel bypasses the blocked coronary artery, circumventing the occlusion and restoring adequate blood flow to the heart muscle. This treatment is known as a coronary artery bypass graft procedure (CABG). A CABG procedure can be performed on a stopped heart, where the patient has been placed on a heart-lung machine, or on a beating heart. Access to the thoracic cavity for a CABG procedure can be provided by sawing the sternum and opening the chest, or by creating one or more small openings in the thoracic cavity. Anastomosis may be performed by hand-suturing the graft vessels together or by utilizing an anastomosis device.

Regardless of the type of CABG procedure that is performed, or the type of anastomosis performed, an opening is made in the aorta or other artery at the proximal anastomosis site to allow blood to flow into the graft vessel. Typically, an incision is made in the aorta with a scalpel. A distal end of an aortic punch is inserted into the incision, then actuated to cut a larger opening in the aorta. While the combination of the scalpel and the aortic punch is commonly used to form an opening in the aorta, there are drawbacks. Between the time the incision is made and the time the aortic punch is used, it is difficult to maintain hemostasis. For example, the surgeon may place a finger over the incision after it is made. This is a problematic approach that does not provide reliable hemostasis during beating heart surgery, and has the potential to allow the location of the incision to become lost. Further, after the aortic punch creates an opening in the aorta, blood will flow out of that opening. Further, the aortic punch is just one tool of a multiple-tool system for creating an opening in the aorta. At least one additional tool is needed for attaching a graft vessel to a target vessel. The use of multiple tools adds steps, time and complexity to the CABG procedure.

Other tools for creating an opening in a blood vessel wall utilize piercing members in conjunction with a cutter, where the piercing member and cutter are free to move relative to one another, and are actuated separately. The piercing member is generally deployed first, followed by the cutter. However, such an arrangement of the piercing member and the cutter can have difficulties in successfully creating a smooth opening in the blood vessel wall, and can have problems in retaining the tissue plug after it is removed from the blood vessel wall. Further, such an arrangement of the piercing member and cutter can be mechanically complex to implement.

SUMMARY

In one aspect of the invention, an auger is fixed relative to a cutter. The auger is positioned within the cutter, which may have a tubular structure. Because the auger and the cutter are fixed to one another, they rotate and advance together to penetrate the wall of a tubular vessel and cut tissue from it. The auger and the cutter are then retracted from the vessel wall. The auger retains the tissue within the cutter so that it can be removed from the vessel wall. The auger and the cutter thus create an opening in the vessel wall, without the need for a prior incision in that wall.

In another aspect of the invention, the auger and the cutter translate together but are free to rotate relative to one another. That is, the auger and the cutter are fixed with respect to translation, but not with respect to rotation. The auger and cutter are advanced together into the vessel wall, while one rotates and the other does not, or while both rotate at different rates or in different directions.

In another aspect of the invention, the cutter is vented to allow fluid such as air or blood to escape from it as the cutter and auger enter the wall of the tubular vessel. In this way, fluid does not become trapped within the cutter during operation, where it could create pressure that acts against the tissue of the vessel wall to oppose its entry into the cutter.

In another aspect of the invention, the cutter and auger are advanced into the wall of a tubular vessel through and ahead of an introducer having an internal diameter substantially the same as the outer diameter of the cutter. The distal end of the introducer enters the opening in the vessel wall as it is made, and remains in the opening after the auger and cutter are retracted, substantially sealing against the sides of the opening. The introducer, in combination with a seal housing or other plenum or structure connected to it, can thereby substantially maintain hemostasis both during and after creation of the opening.

In another aspect of the invention, the auger is part of an auger assembly. An actuator is attached to the auger assembly. The actuator is capable of rotational and translational motion. Because the cutter is fixed to the auger assembly, rotary and/or translational motion of the actuator causes corresponding motion of both the auger assembly and the cutter.

In another aspect of the invention, the auger assembly and cutter are rotated and advanced impulsively when stored energy is applied to them. The auger assembly and cutter are connected to an impulse source, such as a spring, via the actuator or other mechanism. The tissue of the tubular vessel may be strain rate sensitive, such that it is easier to cut when the cutting is performed rapidly than when it is performed slowly. By deploying the auger and cutter impulsively, they move rapidly to better cut strain rate sensitive tissue. In this way, the auger and cutter rapidly and accurately cut tissue from the wall of the tubular vessel.

In another aspect of the invention, the impulse source releases stored energy by rotating a first shaft. The first shaft is connected to a second shaft by gears, such that rotation of the first shaft causes rotation of the second shaft. The second shaft is threaded across a portion of its length, and that threaded portion is received in a threaded opening in a fixed structure. The threads are configured to translate the second shaft distally in response to the rotation of the first shaft. Thus, rotation of the first shaft is converted into both rotation and translation of a second shaft that is connected to the actuator, which in turn is connected to the auger assembly and/or the cutter.

In another aspect of the invention, a registration member is placed against the tubular vessel at an intended anastomosis site without substantially flattening it. The auger and cutter advance distally a fixed amount relative to the registration member. This fixed amount is selected to prevent the auger and cutter from translating completely across the diameter of the lumen of the tubular vessel and contacting its back wall.

In another aspect of the invention, rotational motion of a control assembly operatively connected to the auger assembly and the cutter controls the rotation and advancement of the auger assembly and cutter. This control assembly may include a cam cylinder having at least one cam path defined therein, a knob connected to the cam cylinder, and/or different or additional elements. The control assembly is configured to deploy the auger and cutter into tissue at a particular point in its rotational motion. The control assembly is operationally connected to an introducer tube and other associated components as well.

BRIEF DESCRIPTION OF THE DRAWINGS

The use of the same reference symbols in different figures indicates similar or identical items.

DETAILED DESCRIPTION

Figure 1:
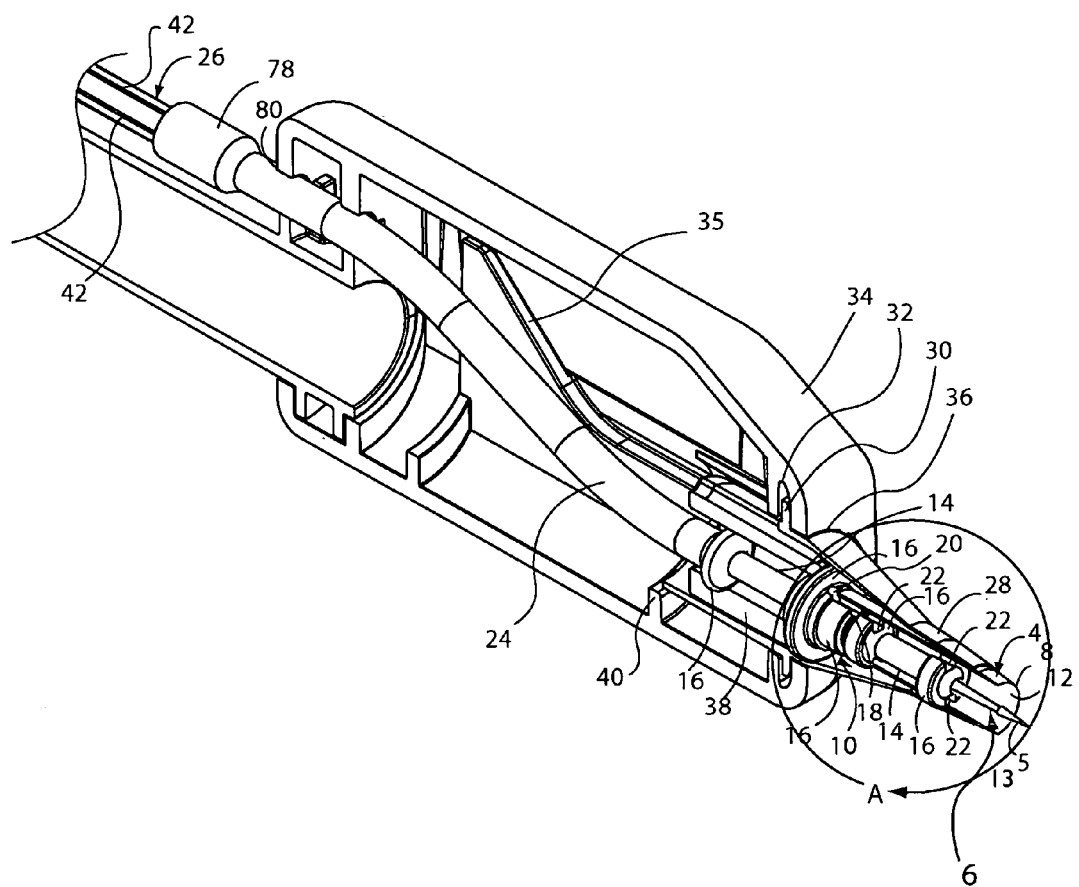
FIG. 1 is a cutaway view of the distal end of an assembly for creating an opening in the wall of a tubular vessel.
Figure 2:
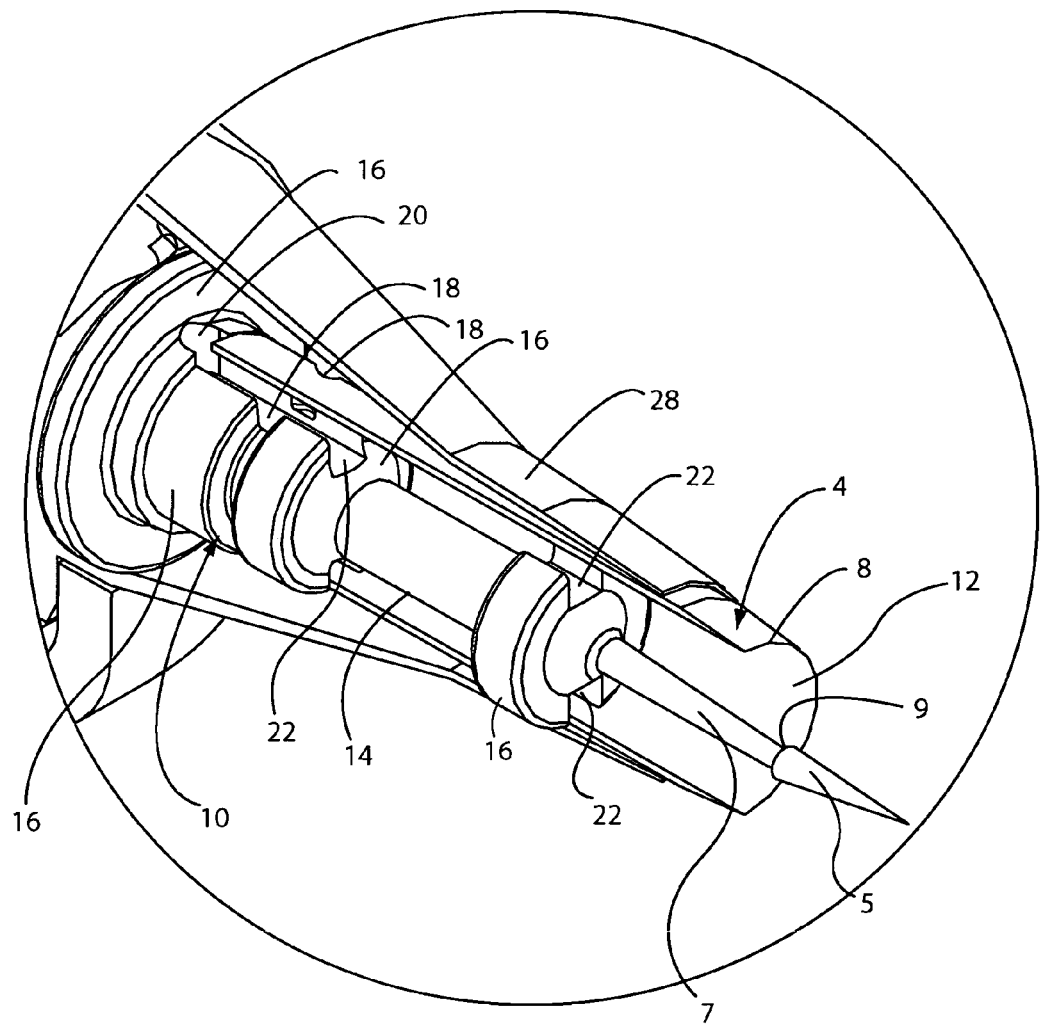
FIG. 2 is a detail view of the distal end of the assembly of FIG. 1.
Figure 3:
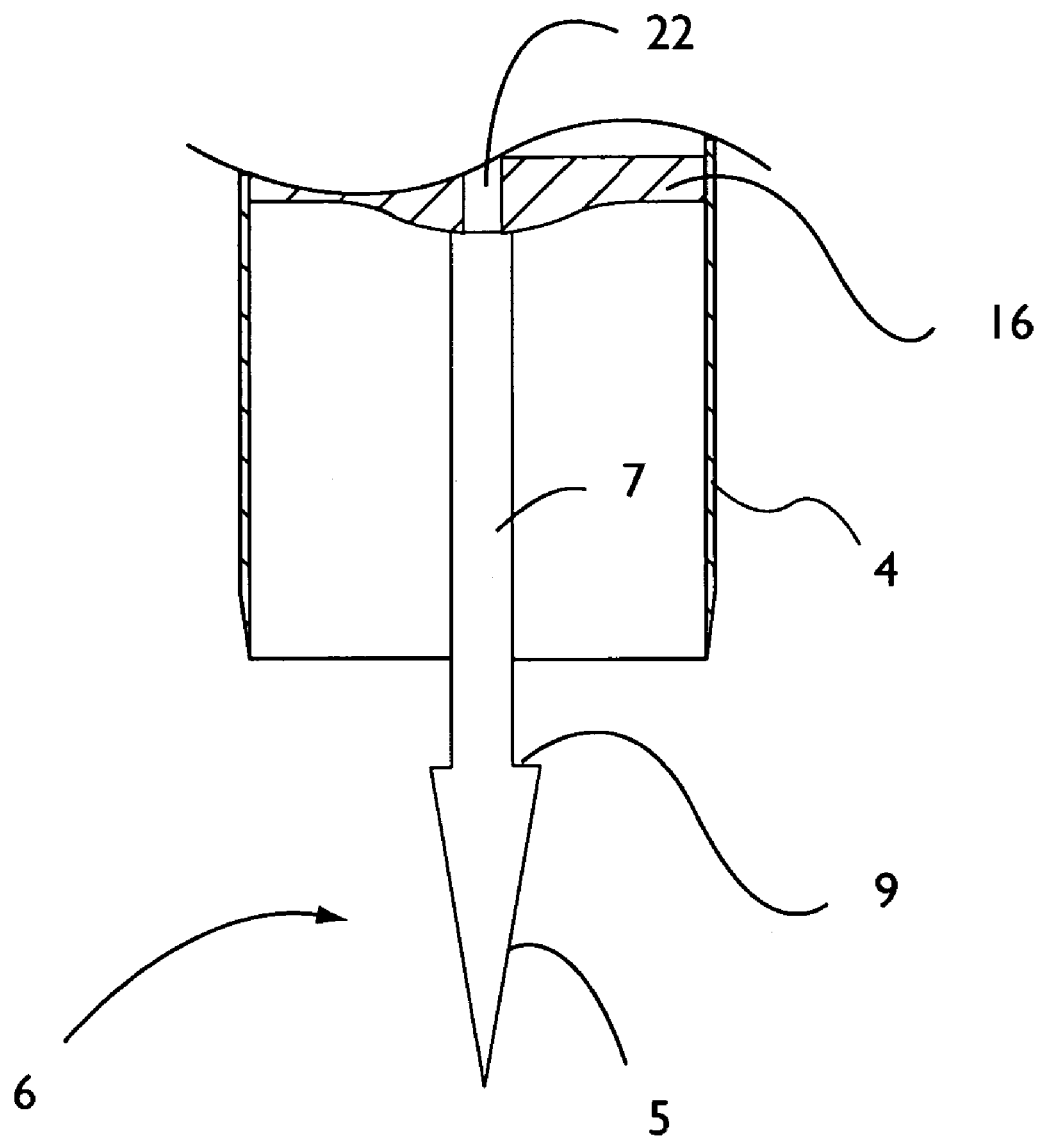
FIG. 3 is a cross-section detail view of an auger and cutter forming part of the assembly of FIGS. 1 and 2.

Referring to FIGS. 1-3, a cutter 4 is connected to an auger 6. The cutter 4 and auger 6 may be part of an integrated anastomosis tool. Alternately, the cutter 4 and auger 6 may be part of a stand-alone cutting tool, or a different tool or mechanism. The cutter 4 is constructed from a biocompatible metal, such as stainless steel, but a different biocompatible material may be used if desired. The distal end of the cutter 4 is sharpened to cut the wall of a tubular vessel, such as the aorta or other blood vessel. The cutter 4 is a hollow tubular structure with an open distal end. The distal end of the cutter 4 has a substantially circular shape, and the cutter 4 has a substantially circular cross-section along its length. However, the cutter 4 may take another shape, have a different cross section, or vary in cross section along its length. For example, the cutter 4 may take the shape of a tube having an open slit along its length. That is, the cutter 4 may form of the majority of a cylindrical surface, where the cutter 4 extends along, for example, 350° of the complete 360° perimeter of the cylinder. The cutter 4 has an inner surface 12 and an outer surface 8. The distal end of the cutter 4 is beveled for sharpness. The distal end of the cutter 4 may be beveled inward, such that the inner surface 12 contacts a vessel wall before the outer surface 8, or beveled outward, such that the inner surface 12 contacts a vessel wall after the outer surface 8. Alternately, the distal end of the cutter 4 may be beveled both inward and outward, such that a sharp edge is provided at a location between the inner surface 12 and outer surface 8 of the cutter 4.

The auger assembly 10 is fixed to the cutter 4, and extends through its hollow center. In one embodiment, the auger assembly 10 extends through at least part of the hollow center of the cutter 4, and extends to a location proximal to the proximal end of the cutter 4. The auger assembly 10 is constructed from the same biocompatible metal as the cutter 4. Alternately, the auger assembly 10 may be constructed from a different biocompatible material. The auger assembly 10 may include a number of components. The auger 6 is one of these components, located at the distal end of the auger assembly 10. The auger 6 may be an integral part of the auger assembly 10, or instead may be a separate component that is connected to another portion of the auger assembly 10. Referring particularly to FIG. 3, the auger 6 is substantially coaxial with the cutter 4. The auger 6 includes a spike 5 at its distal end, and a shaft 7 extending proximally from the spike 5. The shaft 7 is substantially cylindrical. Alternately, the shaft 7 may be shaped differently. The spike 5 is tapered from its proximal end toward its distal end, and is substantially radially symmetrical. The distal end of the spike 5 is sharp to allow it to readily penetrate tissue, as described in greater detail below. The proximal end of the spike 5 is wider than the shaft 7, such that a ledge 9 is formed at the proximal end of the spike 5. The distal end of the spike 5 extends distal to the distal end of the cutter 4. Further, the spike 5 is positioned relative to the cutter 4 and is shaped such that the ledge 9 extends distally at least as far as the distal end of the cutter 4.

Alternately, the auger 6 and the cutter 4 are configured as described above, but are fixed to one another only axially; they are free to rotate with respect to one another. That is, the auger 6 and cutter 4 are configured to translate together at the same rate in the axial direction, but are free to rotate independently of one another. For example, the auger 6 may include a circumferential flange (not shown) held within a corresponding groove (not shown) in the cutter 4. The flange can rotate within the groove 4, and contact between the flange and the groove causes the auger 6 and cutter 4 to translate together. That is, the auger 6 and the cutter 4 are fixed axially, but independent rotationally. While the auger 6 and the cutter 4 are capable of rotating relative to one another, they need not do so, and may rotate together at the same rate if desired. Other mechanisms or structures may be used to configure the auger 6 and the cutter 4 to translate together axially while having the capability of rotating independently.

Figure 4:
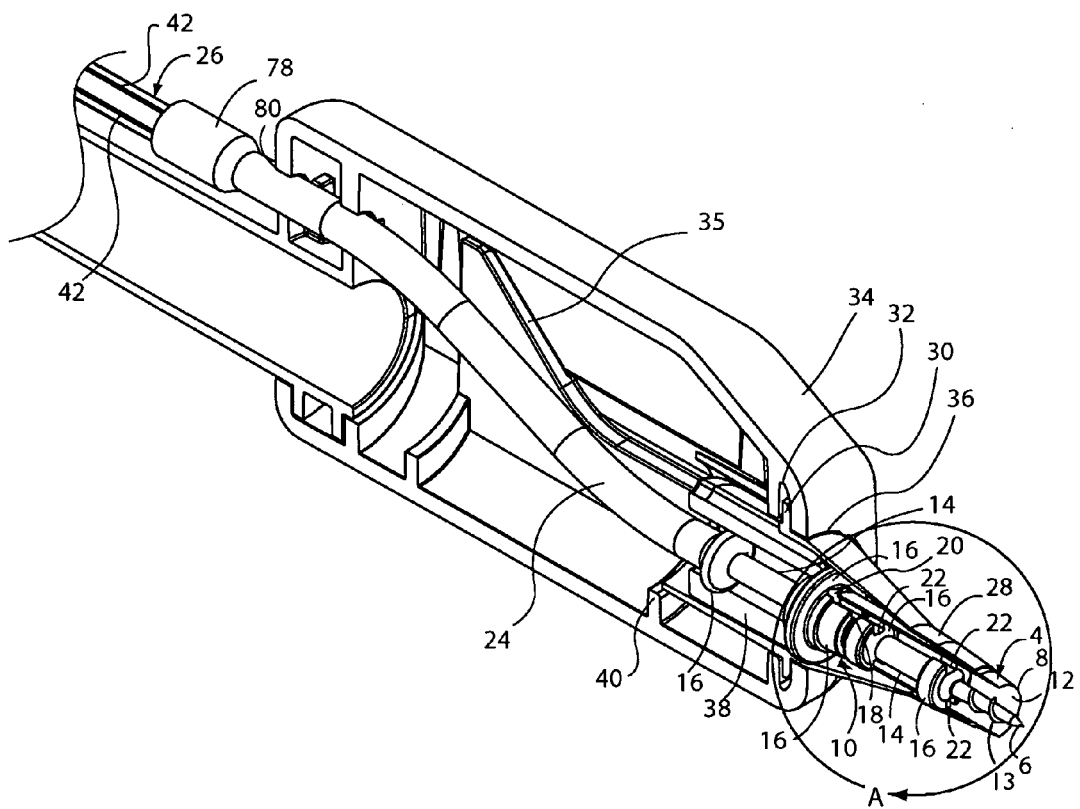
FIG. 4 is a cutaway view of the distal end of another embodiment of assembly for creating an opening in the wall of a tubular vessel.
Figure 5:
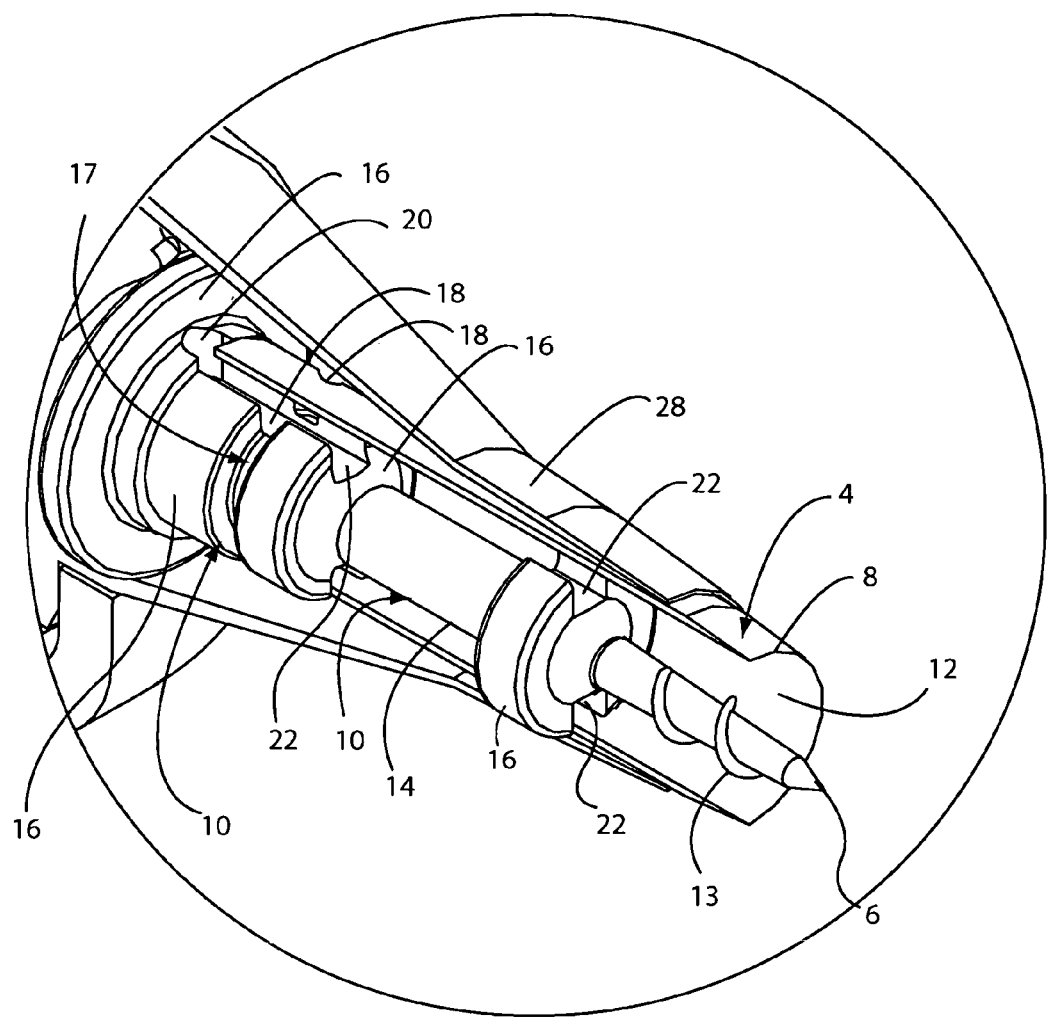
FIG. 5 is a detail view of the distal end of the assembly of FIG. 4.

Referring to FIGS. 4-5, another embodiment of the auger 6 is shown. The auger 6 has one or more flutes 13 defined on its outer surface. The flutes 13 have a pitch of substantially 16 threads per inch and a thread angle of substantially thirty-seven degrees. Alternately, a different pitch and/or thread angle may be used. In one embodiment, the auger 6 is tapered from its proximal end toward its distal end. The distal end of the auger 6 is sharp, to facilitate its entry into the wall of the tubular vessel, and extends to a location that is further in the distal direction than the distal end of the cutter 4. Alternately, a piercing member other than the auger 6 is axially fixed to the cutter 4, such as a barb, harpoon, lance, corkscrew or a needle without flutes.

The auger assembly 10 includes a center rod 14 that is connected to the shaft 7 of the auger 6 and that is substantially coaxial with the cutter 4 and with the auger 6. Alternately, the center rod 14 may be positioned along a different axis. The shaft 7 may be formed as an integral part of the center rod 14. One or more centering flanges 16 are fixed to the center rod 14, extending outward radially from the center rod 14 to contact the cutter 4. One or more of the centering flanges 16 may be fixed to the cutter 4. The centering flanges 16 are utilized to position the center rod 14 within the cutter 4 along at a desired axis and to provide support and stiffness to the cutter 4. As described above, the centering flanges 16 may be utilized to center the center rod 14 within the cutter 4. In one embodiment, the centering flanges 16 are constructed as part of the center rod 14, thereby forming a unitary structure. However, the centering flanges 16 may be constructed separately from the center rod 14, then connected to the center rod 14, such as by adhesive or other fastening mechanism, structure or method. One or more centering flanges 16 may also be formed into or attached to the portion of the center rod 14 that extends proximal to the cutter 4. These centering flanges 16 may be utilized to position the center rod 14 relative to one or more other structures or mechanisms and/or to provide bearing surfaces for rotation of the auger assembly 10. The centering flanges 16 may have different thicknesses in the axial direction.

The cutter 4 is attached to the auger assembly 10 by dimpling the cutter 4 in one or more locations. One of the centering flanges 16 includes a groove 17 defined substantially circumferentially around it. The centering flange 16 that includes the groove 17 may be wider than one or more other centering flanges 16. Each dimple 18 is located within the groove 17. Each dimple 18 is formed by pressing the cutter 4 inward toward the groove 17, causing that location on the cutter 4 to deform into a dimple 18. The dimple 18 expands into a portion of the groove 17, trapping the dimple 18 therein. The cutter 4 thus is fixed to the auger assembly 10, such that they rotate and translate together. Alternately, the cutter 4 includes one or more partially-circumferential ribs (not shown) extending inward from its inner surface 12. Each rib is crimped between two centering flanges 16, and is thereby trapped between them and fixed to them to fix the cutter 4 to the auger assembly 10. The auger assembly 10 may be connected to the cutter 4 using other or additional suitable mechanisms, structures or methods. Such a connection may be used where the auger 6 is fixed axially to, but free to rotate relative to, the cutter 4. For example, the auger assembly 10 and the cutter 4 may be molded or otherwise formed together as a single piece. As another example, the auger assembly 10 and the cutter 4 may be fixed together by adhesive. As another example, the auger assembly 10 and the cutter 4 may be fixed together by welding, or may be pinned or screwed together.

At least one vent 20 is defined in the auger assembly 10 at or proximal to the proximal end of the cutter 4. The vent 20 connects a space inside the cutter 4 with a space outside the cutter 4. Similarly, at least one slot 22 is defined through each centering flange 16. If a centering flange 16 is located adjacent to the proximal end of the cutter 4, the slot 22 in that centering flange 16 is aligned with the vent 20. The vent 20, in combination with the at least one slot 22 in each centering flange 16, provides a pathway for fluid such as air or blood to escape from the cutter 4 when the cutter 4 and auger 6 are deployed into the vessel wall. The cutter 4 is vented to prevent fluid from becoming trapped within the cutter 4, because the pressure of that trapped fluid could potentially prevent the cutter 4 from penetrating the vessel wall or other anatomical structure. Other structures or mechanisms than the vent 20 and the slot 22 may be used to vent the cutter 4.

An actuator 24 is connected to the proximal end of the auger assembly 10. The center rod 14 extends to the proximal end of the auger assembly 10, and the actuator 24 connects to the center rod 14. Advantageously, the actuator 24 is a coil spring that is tightly wound, and the center rod 14 is threaded into the distal end of the spring. Alternately, the spring may be connected to the center rod 14 by adhesive, welding, soldering, compressive force or other methods or mechanisms. In this way, the spring provides flexibility and transmits translational and rotational force to the auger assembly 10. However, the actuator 24 may be any other structure or mechanism that is capable of transmitting translational and rotational forces to the auger assembly 10. Additionally, the actuator 24 need not be flexible if the auger 6 and cutter 4 are not moved off-axis, as is described in greater detail below. The actuator 24 is connected at its proximal end to the distal end of a first driveshaft 26.

At least a portion of the auger assembly 10 and the cutter 4 is positioned within a hollow introducer tip 28. The introducer tip 28 is a tapered element that is narrower at its distal end than at its proximal end. Alternately, the introducer tip 28 is not tapered. The introducer tip 28 has a substantially circular cross-section along its length. The introducer tip 28 is a radially and bilaterally symmetrical shell. Alternately, the introducer tip 28 can take a different shape, symmetry or form. The introducer tip 28 is composed of a biocompatible plastic, although a different material or combination of materials may be used. The inner diameter of the distal end of the introducer tip 28 is substantially the same as the outer diameter of the cutter 4, as measured at the distal end of the introducer tip 28. Further, the introducer tip 28 is substantially coaxial with the cutter 4. Thus, at the distal end of the introducer tip 28, the cutter 4 substantially seals against the introducer. As with the distal end of the cutter 4, the distal end of the introducer tip 28 may be beveled inward. Initially, the cutter 4 extends distally from the distal end of the introducer tip 28, and the distal end of the introducer tip 28 follows the cutter 4 into an opening cut in the wall of a tubular vessel, as is described in greater detail below. The introducer tip 28 may be splittable or expandable, if desired, such that the diameter of its distal end can be enlarged. Such enlargement may be useful in translating an anastomotic device through the introducer tip 28, or for other purposes.

The introducer tip 28 includes a circumferential flange 30 at or near its proximal end, where that flange 30 is held within a circumferential slot 32 in a seal housing 34 at or near its distal end. The introducer tip 28 thereby is secured to the seal housing 34. Alternately, the flange 30 is not circumferential, and the slot 32 in the seal housing 34 is correspondingly not circumferential. Alternately, the introducer tip 28 is secured to the seal housing 34 by a different structure, mechanism or method, such as by adhesive. The seal housing 34 is a substantially hollow structure into which the proximal end of the auger assembly 10 extends. The seal housing 34 includes an opening 36 at or near its distal end through which the introducer tip 28 and the auger assembly 10 extend. The cutter 4 extends proximally through the opening 36 in the seal housing 34. Alternatively, the cutter 4 does not extend as far proximally as the opening 36 in the seal housing 34. The actuator 24 extends through the seal housing 34, and may extend out of an opening 40 at or near the proximal end of the seal housing 34. Alternately, the actuator 24 does not extend out of the seal housing.

The proximal end of the auger assembly 10 extends through the interior of a bushing 38. The bushing 38 is substantially cylindrical and has a substantially cylindrical opening therethrough. However, the bushing 38 and/or the opening through it may be shaped differently. The distal end of the bushing 38 contacts at least one centering flange 16 that is connected to the center rod 14. The distal end of the bushing 38 may be free to translate relative to that centering flange 16, where that centering flange 16 has a diameter larger than the passage through the bushing 38 such that the bushing 38 cannot advance distally past that centering flange 16. Alternately, the distal end of the bushing 38 contacts the inner surface of the introducer tip 28 instead of or in addition to at least one centering flange 16. The bushing 38 is restrained from rotation as the cutter 4 and auger assembly 10 rotate due to contact with at least one centering flange 16 and/or the introducer tip 28. However, registration features, stops or other structures or mechanisms may be used to restrain the bushing 38 from rotation. The bushing 38 may be tapered, such that the distal end of the bushing 38 contacts at least one centering flange 16, and another, wider location on the bushing 38 near the distal end of the bushing 38 contacts the inner surface of the introducer tip 28. The bushing 38 is supported by the introducer tip 28. The proximal end of the bushing 38 may contact a rib 40 or other structure within the seal housing 34. However, the proximal end of the bushing 38 is not fixed to the rib 40 or similar structure. Thus, the bushing 38 is free to translate proximally with respect to the introducer tip 28, but is restrained in its forward motion by contact with at least one centering flange 16 and/or introducer tip 28. One or more centering flanges 16 may be located within the bushing 38, and each centering flange 16 is connected to the center rod 14. However, the centering flanges 16 within the bushing 38 are free to rotate relative to the bushing 38. Thus, the auger assembly 10 may rotate relative to the bushing 38, and is supported and guided by the bushing 38 during this rotation.

A guide 35 is defined in or connected to the inner surface of the seal housing 34. The guide 35 may be a ramp, slot or other structure or mechanism. Advantageously, two guides 35 are provided, one on the inner surface of each side of the seal housing 34. For clarity, only one side of the seal housing 34 is shown. Because the seal housing 34 is substantially symmetrical, the guide 35 on the side of the seal housing 34 that is not shown is substantially symmetrical with the guide 35 shown. A guide follower (not shown) extends from the bushing 38 to contact or otherwise engage the corresponding guide 35. One guide follower is associated with each guide 35. The guides 35 are configured to guide the bushing 38, and with it the auger 6, cutter 4 and captured tissue away from the axis of the introducer tip 28 to a second axis spaced apart from the introducer axis, as is described in greater detail below. Thus, the location and orientation of the guides 35 on the inner surface of the seal housing 34 is dependent upon the location of the second axis.

Figures 6, 7:
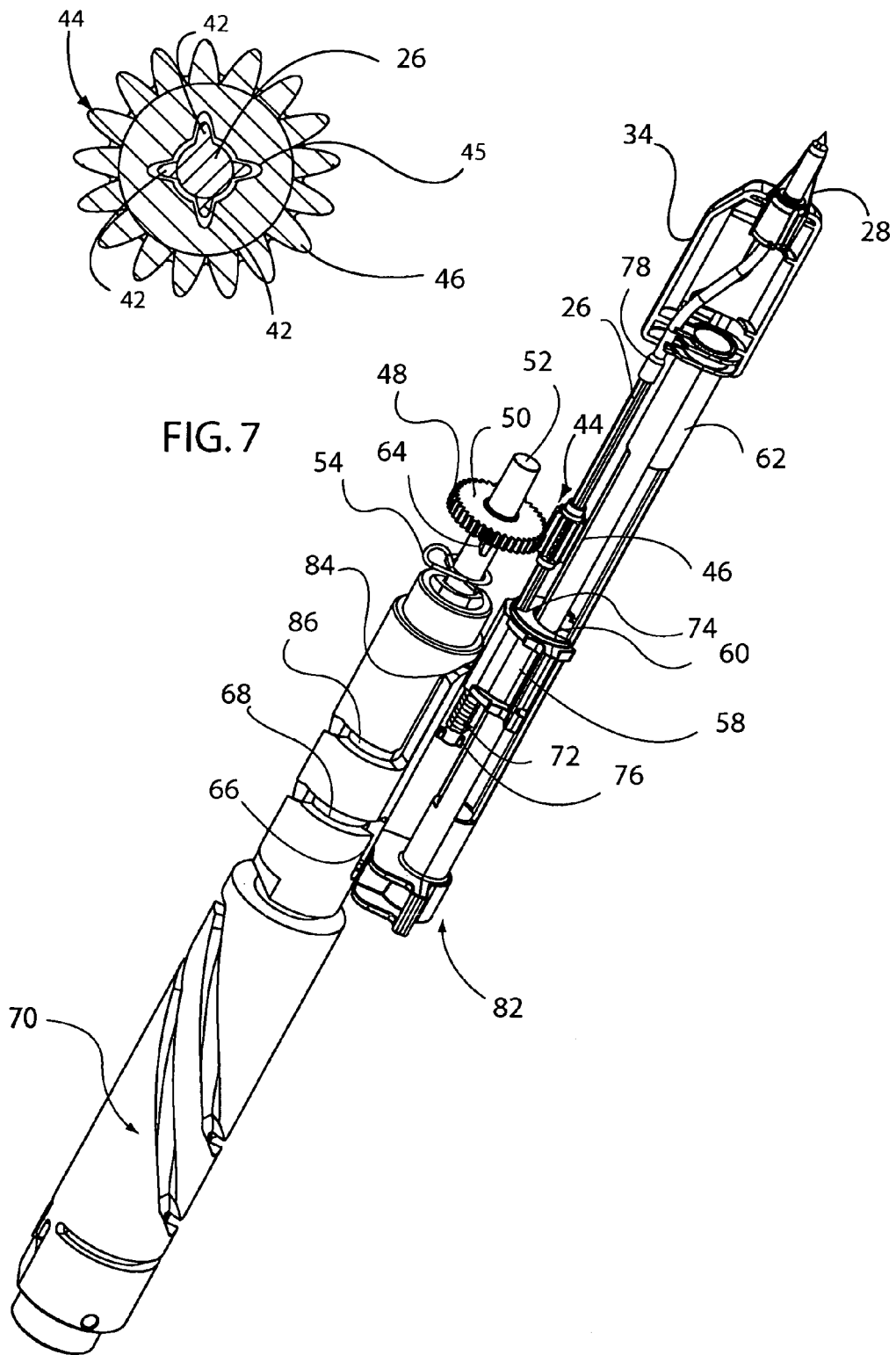
FIG. 6 is a perspective view of a drive mechanism for use with the assembly for creating an opening in the wall of a tubular vessel.
FIG. 7 is an end cross-section view of a first gear and a first driveshaft forming part of the drive mechanism of FIG. 6.

The auger assembly 10 and the cutter 4 can be actuated to rotate and to translate forward in any one of a number of ways. Referring also to FIG. 6, the distal end of a first driveshaft 26 is connected to the proximal end of the actuator 24. The connection between the first driveshaft 26 and the actuator 24 may be made inside or outside the seal housing 34. The first driveshaft 26 is substantially rigid, and has a number of ribs 42 aligned substantially axially along its surface, extending substantially radially outward. Alternately, the ribs 42 are aligned and/or extend differently. Four ribs 42 are spaced evenly around the circumference of the first driveshaft 26, but more or fewer ribs 42 may be utilized. The first driveshaft 26 is capable of axial translation relative to a first gear 44 that is substantially coaxial with the first driveshaft 26. The first gear 44 is mounted to a casing (not shown) or other structure, such that it is free to rotate about its axis but fixed in the axial direction and restrained against axial translation. Such mounting is standard in the art. The first gear 44 has a passage 45 therethrough, wherein a number of ribs (not shown) extend inward toward the rod 24 and are positioned between the ribs 42 on the first driveshaft 26. Contact between the ribs 42 and at least a portion of the surface of the passage 45 allows the first driveshaft 26 to translate axially relative to the first gear 44. Alternately, the first gear 44 and the first driveshaft 26 may be configured differently to allow rotary motion to be transmitted between the first driveshaft 26 and the first gear 44 while additionally allowing the first driveshaft 26 to translate axially relative to the first gear 44.

Figure 8:
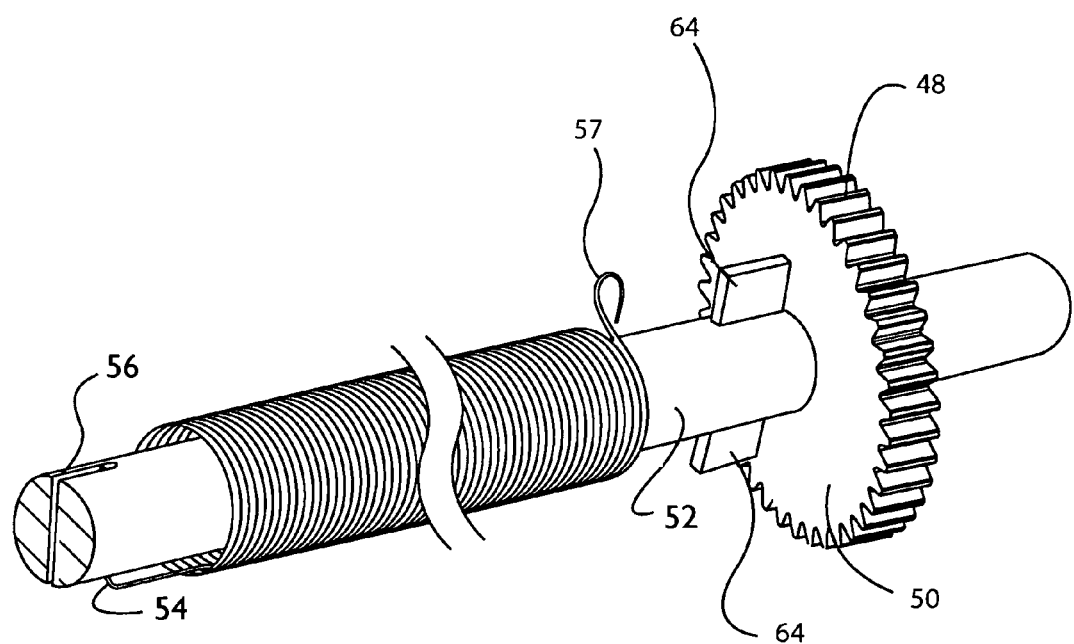
FIG. 8 is a perspective view of a second driveshaft forming part of the drive mechanism of FIG. 6.

Referring also to FIGS. 6-8, the first gear 44 has a number of teeth 46 aligned in a substantially axial direction and extending outward substantially radially. These teeth 46 interface with teeth 48 of a second gear 50, which correspondingly extend in a substantially axial direction. The second gear 50 has a diameter larger than that of the first gear 44, such that the gear ratio between the second gear 50 and the first gear 44 is larger than 1:1. Advantageously, the gear ratio is substantially 39:11. A different gear ratio may be used, if desired. The second gear 50 is mounted substantially coaxially to a second driveshaft 52 that is substantially parallel to the first driveshaft 26. Alternately, the second driveshaft 52 may be positioned in another orientation, and the teeth of the gears 44, 50 are constructed to interface at that orientation. Rotation of the second driveshaft 52 at a particular rate causes the first driveshaft 26 to rotate at a faster rate, due to the gear ratio of greater than 1:1 between the second gear 50 and the first gear 44.

The second driveshaft 52 may be driven by any mechanism or method. In one embodiment, the second driveshaft 52 is connected to an impulse source. A force that acts on a body for a short time but produces a large change in its linear or angular momentum is called an impulsive force. As used in this document, the term "impulse source" refers to a source of such an impulsive force. The impulse source is a torsional spring 54. However, the impulse source instead may be a different mechanism. The duration of the force generated by the spring 54 or other impulse source is substantially 0.05 seconds. However, the duration may be shorter or longer. Referring particularly to FIG. 8, the spring 54 surrounds at least a portion of the length of the second driveshaft 52. The proximal end of the spring 54 is fixed to a slot 56 in the second driveshaft 52. FIG. 8 shows a cross-section of the second driveshaft 52 for clarity in illustrating the connection between the spring 54 and the slot 56. The proximal end of the spring 54 is bent to fit into the slot 56, and is stiff enough and extends into the slot 56 far enough such that the contact between the proximal end of the spring 54 and the slot 56 holds the spring 54 in place. Alternately, the proximal end of the spring 54 is fixed to the second driveshaft 52 in another way. The distal end 57 of the spring 54 extends outward from the second driveshaft 52, and is fixed to a casing (not shown) or other structure relative to which the second driveshaft 52 rotates. Before the auger assembly 10 and cutter 4 are actuated, the spring 54 is wound up tightly, thereby storing a quantity of force in a torsioned state.

The impulse source may be different from the spring 54. For example, the impulse source may be a DC motor connected directly or via one or more gears to the second driveshaft 52. As another example, the impulse source may be a flow of biocompatible liquid such as water through an impeller or other mechanism connected to the second driveshaft 52. As another example, the impulse source is a magnetic field source coupled to the second driveshaft 52. A different impulse source than these exemplary ones may be used instead. In another embodiment, the impulse source is not used, and the auger assembly 10 and the cutter 4 are rotated non-impulsively, such as by hand.

One or more registration features 64 extend substantially radially outward from the second driveshaft 52 and/or the second gear 50. Each registration feature 64 is a tab. Alternately, the registration features 64 may be different structures than tabs. Where multiple registration features 64 are used, they are spaced evenly around the axis of the second driveshaft 52, but may be spaced differently if desired. Thus, where two registration features 64 are used, they are located on opposite sides of the second driveshaft 52, such that they fall substantially in the same plane. Alternately, the registration features 64 are not coplanar. If the registration features 64 are connected to the second gear 50, they are short enough such that they do not interfere with the operation of the second gear 50.

The registration features 64 are held by, or held relative to, the casing (not shown) or other structure or mechanism until rotation of the second driveshaft 52 is desired. Any appropriate structure or mechanism may be used to hold the registration features 64 relative to the casing. As one example, each registration feature 64 is positioned in a slot (not shown) defined by raised features on the inner surface of the casing, or against a ridge (not shown) extending inward from the casing toward the second driveshaft 52. The slots, ridges or other structures or mechanisms engage the registration feature or features 64 and restrain the second driveshaft 52 against rotation. Where the impulse source is the spring 54, the spring 54 biases the registration features 64 against the corresponding slots, ridges or other structures used to restrain the registration features 64. The registration features 64 are freed from the corresponding slots, ridges or other structures or mechanisms in order to allow rotation of the second driveshaft 52. For example, a slot holding a registration feature 64 is open at its distal end. Motion of the registration feature 64 distally frees it from the slot, allowing the second driveshaft 52 to rotate under the influence of the impulse source. As another example, a ridge holding a registration feature 64 extends axially. Motion of the registration feature 64 distally moves it beyond the ridge, allowing the second driveshaft 52 to rotate under the influence of the impulse source. Freeing the registration features 64 may be accomplished in a different manner, if desired.

As shown in FIG. 6, the second driveshaft 52 is in an initial position, in which the registration features 64 are restrained by slots, ridges, or other structures or mechanisms (not shown). This position may be referred to as the restrained position. After the second driveshaft 52 advances distally to free the registration features 64, the second driveshaft 52 is in a second position that may be referred to as the deployed position. The second gear 50 is fixed to the second driveshaft 52, such that the second gear 50 advances distally the same distance as the second driveshaft 52. The first gear 44 is at least as long as the distance that the second gear 50 advances, such that the first gear 44 is in mating contact with the second gear 50 throughout the entire distance that the second gear 50 translates.

The registration features 64 described above need not be used if the impulse source does not exert a force against the second driveshaft 52 until rotary motion of the second driveshaft is desired. For example, where the impulse source is a DC motor, the motor may be configured to exert a rotational force on the second driveshaft 52 only when rotary motion of the second driveshaft 52 is desired, and registration features 64 thus need not be provided to restrain the second driveshaft 52 against rotation in the initial position.

Figure 9:
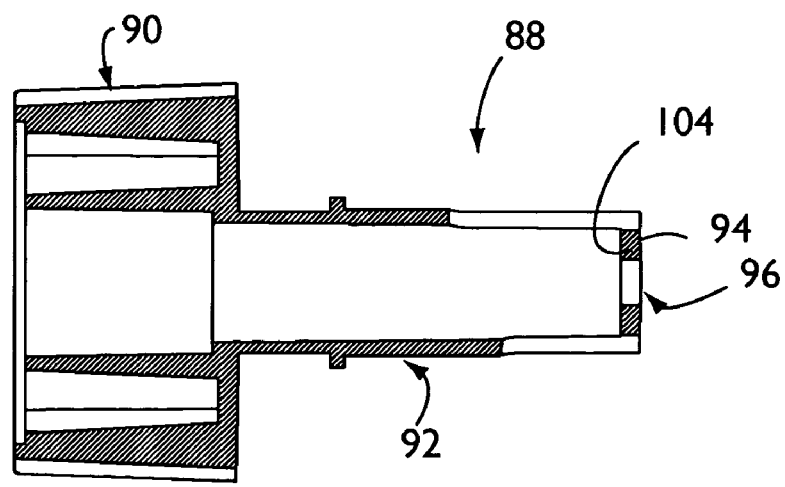
FIG. 9 is a cross-section view of a knob utilized to operate the drive mechanism of FIG. 6.
Figure 10:
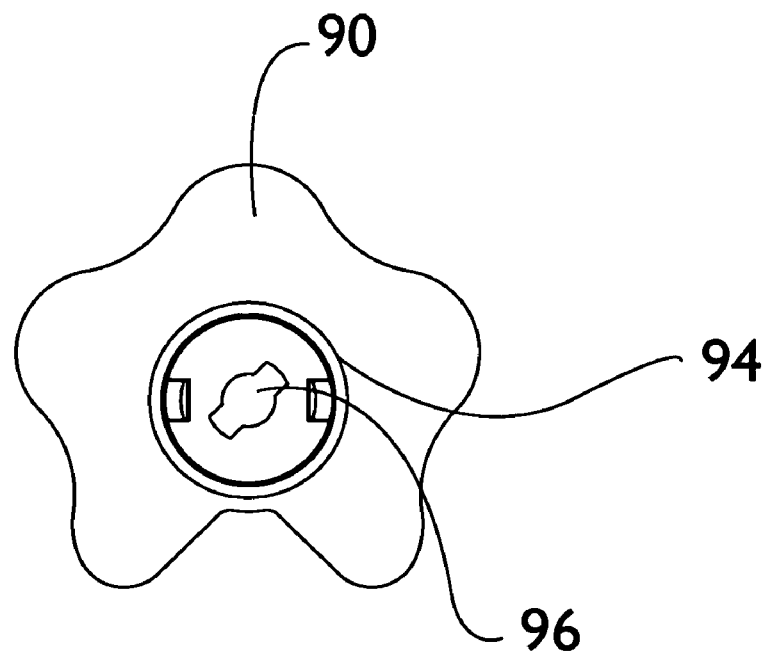
FIG. 10 is an end view of the knob of FIG. 9.
Figure 11:
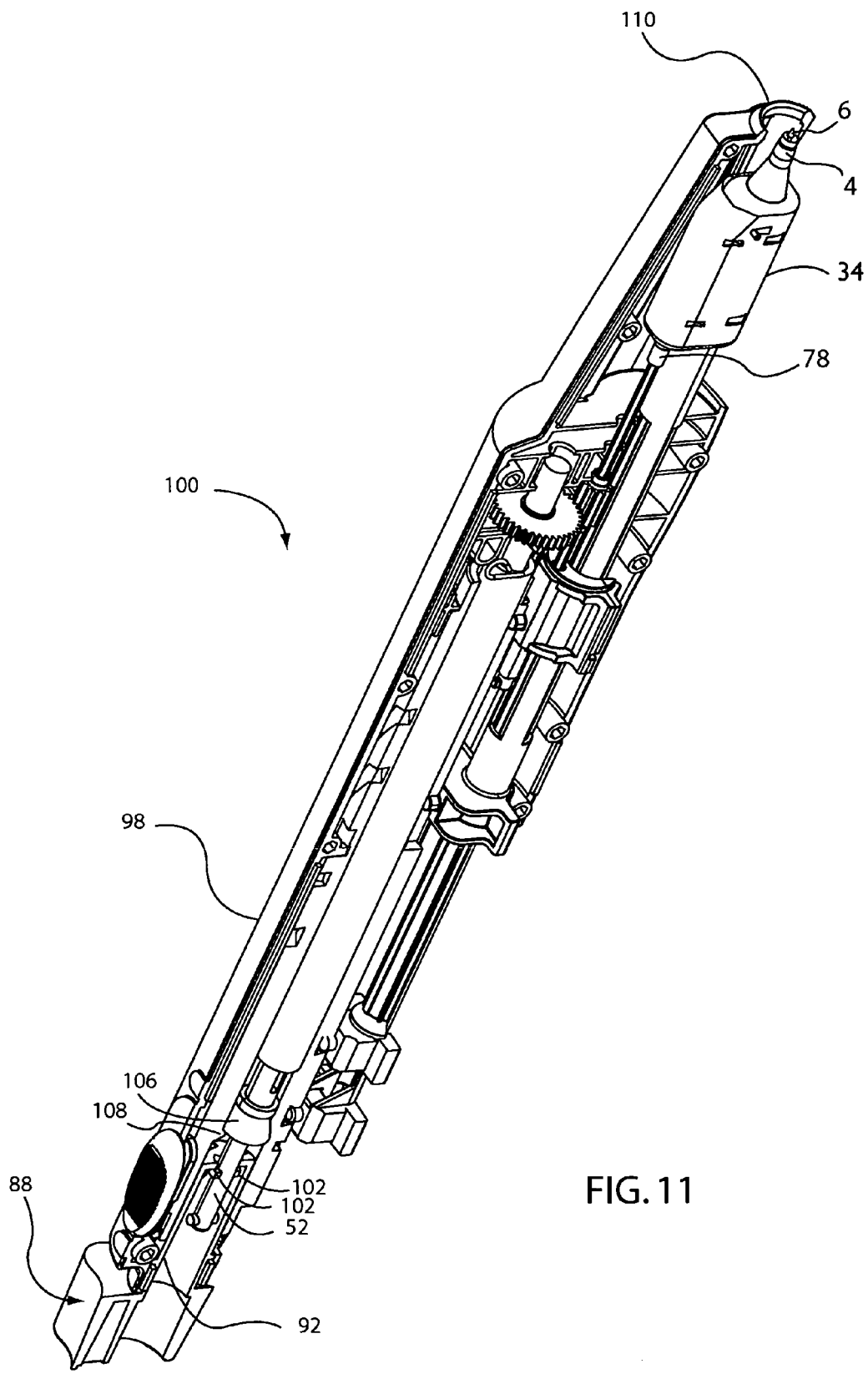
FIG. 11 is a cutaway view of an integrated anastomosis tool, where the tool is in an initial state.

Referring also to FIGS. 9-10, an exemplary embodiment of a knob 88 is shown, where the knob 88 is a component of an integrated anastomosis tool 100. The integrated anastomosis tool 100 is one example of a tool that utilizes and operates the auger 6 and cutter 4. The knob 88 includes a grip 90 and a hollow shaft 92. An endplate 94 is connected to the distal end of the shaft 92. The grip 90, shaft 92 and endplate 94 may be formed as a single piece, as by injection molding or another process. A slot 96 extends through the endplate 94. Referring also to FIG. 11, the shaft 92 extends into a casing 98. The casing 98 is substantially hollow, and one or more of the components described above in this document may be located within the casing 98. The casing 98 protects such components and assists in integrating them into a single integrated anastomosis tool 100. The slot 96 is shaped to allow the second driveshaft 52 to extend through it, such that the second driveshaft 52 extends distally into the shaft 92 of the knob 88.

Two stops 102 extend outward from opposite sides the second driveshaft 52. The stops 102 are shaped as substantially rectangular solids. Alternately, one or more stops 102 are shaped differently. Optionally, only one stop 102 may be used, or more than two stops 102 may be used, or the two stops 102 may be arranged differently on the second driveshaft 52. The stops 102 are initially positioned within the shaft 92 of the knob 88. The second driveshaft 52 is in the restrained position, as shown in FIG. 11, before deployment of the auger 6 and cutter 4. In this restrained position, the stops 102 are biased against the proximal surface 104 of the endplate 94, because the second driveshaft 52 is biased distally. A tapered compression spring 106 attached at its narrow end to the second driveshaft 52 performs the biasing, although a different structure or mechanism may be used. The narrow end of the compression spring 106 is positioned distal to the wider end of the compression spring 106. The wider end of the compression spring 106 presses against a circumferential ridge 108 defined on the casing 98. In the initial state, the compression spring 106 is compressed against the ridge 108, resulting in a distal biasing force. The compression spring 106 may be composed of rubber or a similar flexible substance. However, a different material may be used instead. The biasing force exerted by the compression spring 106 biases the stops 102 against with proximal surface 104 of the endplate 94 of the knob 88. The stops 102 are oriented such that they are not aligned with the slot 96 in the endplate 106, such that the second driveshaft 52 cannot pass through the slot 96 and thus is restrained against distal motion. Other structures or mechanisms than the compression spring 106 may be used to bias the second driveshaft 52, such as a coil spring or leaf spring.

Figure 12:
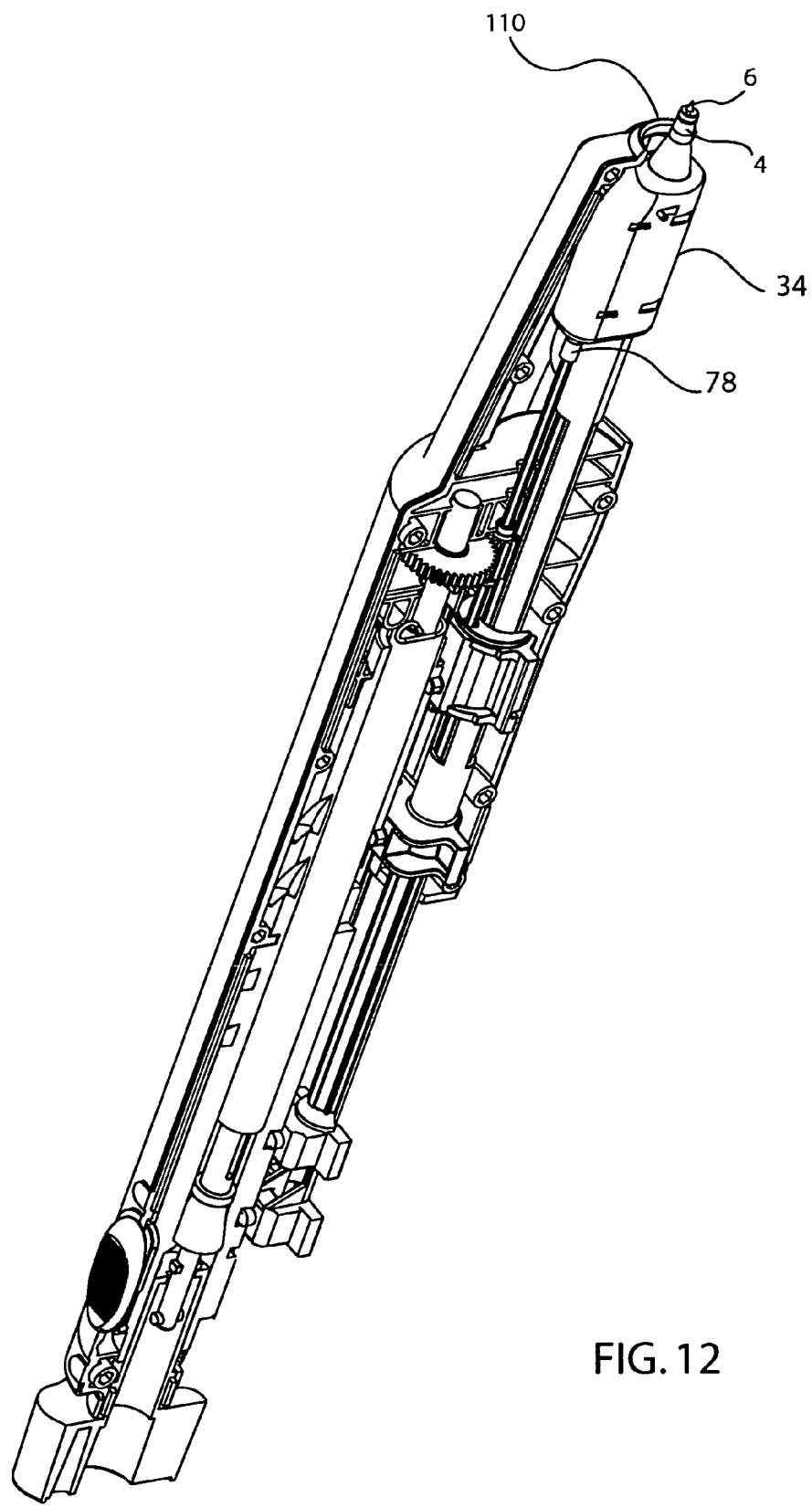
FIG. 12 is a cutaway view of the tool of FIG. 11 in a deployed state.

FIG. 12 shows the second driveshaft 52 in the deployed position, after deployment of the auger 6 and the cutter 4. The knob 88 has rotated, allowing the stops 102 to align with the slot 96 and slide through the slot 96 under the biasing influence of the compression spring 106. The compression spring 106 has moved to a less compressed state. The compression spring 106 may still exert a biasing force distally, but the distal end of the second driveshaft 52, the second gear 50, or another structure or mechanism contacts the casing 98 or another structure and prevents additional forward motion of the second driveshaft 52. The details of the motion of the second driveshaft 52 during operation are described in greater detail below.

Referring back to FIG. 6, the first driveshaft 26 is mounted to a carriage 58. The carriage 58 includes a concave surface 60 on its underside, where that concave surface 60 contacts an introducer tube 62. The introducer tube 62 is a hollow tube fixed to the seal housing 34, having a lumen that opens into the interior of the seal housing 34. That lumen may be substantially coaxial with the axis of the introducer tip 28. Alternately, the lumen of the introducer tube 62 may have an axis parallel to but not coaxial with, or not parallel to, the axis of the introducer tip 28. An anastomosis device (not shown) and vein graft (not shown) may be advanced through the lumen of the introducer tube 62, such that the anastomosis device can connect the vein graft to a target vessel after the auger 6 and cutter 4 have removed a tissue plug from the wall of the target vessel and created an opening therein.

The first driveshaft 26 includes a threaded portion 72 at or near the proximal end of the first driveshaft 26. Alternately, the threaded portion 72 of the first driveshaft 26 is located at another position on the first driveshaft 26. A passage 74 through the carriage 58 is correspondingly threaded to engage the threaded portion 72 of the first driveshaft 26. The threaded portion 72 of the first driveshaft 26 is configured to advance distally as the first driveshaft 26 rotates. Thus, rotary motion of the first driveshaft 26 is used to advance the first driveshaft 26, such that rotation of the second gear 50 is converted to both rotation and translation of the first driveshaft 26. Thus, the threaded portion 72 of the first driveshaft 26 is at least as long as the distance the first driveshaft 26 is to advance, and the corresponding threaded portion of the passage 74 through the carriage 58 can be any length that is capable of adequately supporting the first driveshaft 26 during its advancement. Alternately, the threaded portion 72 of the first driveshaft 26 is shorter than the distance the first driveshaft 26 is to advance, and the threaded portion of the passage 74 through the carriage 58 is at least as long as the distance the first driveshaft 26 is to advance. The threads of the threaded portion 72 of the first driveshaft 26 have a pitch of substantially 25 threads per inch. A different pitch may be utilized, if desired.

The first driveshaft 26 includes a head 76 at or near its proximal end. Alternately, the head 76 is located at a different position on the first driveshaft 26. The head 76 is a structure that is wider than the passage 74 through the carriage 58, such that contact between the head 76 and the carriage 58 stops the distal advancement of the first driveshaft 26. Thus, the head 76 limits the distal travel of the first driveshaft 26. Contact between the head 76 and the carriage 58 provides a positive stop after a particular amount of distal travel of the first driveshaft 26.

Alternately, the first driveshaft 26 does not include a threaded portion 72, and rotation of the second gear 50 causes the first driveshaft 26 to rotate but does not advance the first driveshaft 26 distally. In such an embodiment, a second impulse source (not shown) may be provided, and connected to the carriage 58 or first driveshaft 26 to advance the first driveshaft 26 substantially axially. The second impulse source may be a spring or other mechanism for storing energy and releasing it over a short interval of time. The second impulse source is coordinated with the first impulse source, such as the spring 54, such that both impulse sources produce an impulse at substantially the same time in order to produce rotational and translational motion of the auger assembly 10 and the cutter 4.

The timing, advancement and retraction of the auger assembly 10 and the cutter 4 can be controlled in a number of ways. In one embodiment, a cam cylinder 70 is used to control the advancement of the auger assembly 10 and the cutter 4. The knob 88 or other control structure is directly connected to and substantially coaxial with the cam cylinder 70, such that rotation of the knob 88 rotates the cam cylinder 70. The knob 88 instead may be operationally connected to the cam cylinder 70 via gearing or other mechanisms, such that the knob 88 and cam cylinder 70 can be oriented along different axes. Referring to FIG. 11, a first cam follower 66 extends from the introducer tube 62 into a first cam path 68 defined in the cam cylinder 70. The introducer tube 62 is restrained by the casing 98 and/or other structure or mechanism such that its motion is substantially linear along its axis. Consequently, the first cam follower 66 is restrained to move substantially linearly in a direction substantially parallel to the axis of the introducer tube 62. Rotation of the cam cylinder 70 causes the first cam path 68 to move relative to the first cam follower 66. The first cam follower 66 follows the first cam path 68, and thus can be caused to translate axially or be held stationary as the cam cylinder 70 is rotated. In the initial, restrained position, the first cam follower 66 is prevented from moving substantially distally or proximally by the first cam path 68, because the first cam path 68 is positioned relative to the first cam follower 66 substantially perpendicular to the direction in which the introducer tube 62 can translate, thereby substantially restraining the introducer tube 62 against translational motion. When the cam cylinder 70 is rotated and the first cam follower 66 encounters an segment of the first cam path 68 that extends in a direction having an axial component, the first cam follower 66 is free to translate a selected distance in the axial direction. Consequently, the introducer tube 62 that is connected to the first cam follower 66 is free to translate a selected distance in the axial direction, as is the seal housing 34 that is connected to the introducer tube 62.

Similarly, a second cam follower 84 extends from the carriage 58 into a second cam path 86 defined in the cam cylinder 70. The carriage 58 is restrained by the casing 98, introducer tube 62 and/or other structure or mechanism such that its motion is substantially linear in a direction substantially parallel to the axis of the introducer tube 62. In the initial, restrained position, as well as during translation of the second driveshaft 52, the second cam follower 84 is prevented from moving substantially distally or proximally by the second cam path 86. In that restrained position, the second cam path 86 is positioned relative to the second cam follower 84 substantially perpendicular to the direction in which the carriage 58 can translate, thereby substantially restraining the carriage 58 against translational motion. A segment of the second cam path 86 extends in a direction having an axial component. When the second cam follower 84 encounters such an segment of the second cam path 86, the second cam follower 84 is free to translate a selected distance in the axial direction, as is the carriage 58 that is connected to the second cam follower 84. The components connected to the carriage 58, such as the flexible shaft 24, the auger assembly 10 and the cutter 4, are also free to translate a selected distance in the axial direction. Thus, the motion of the auger assembly 10 and the cutter 4, as well as other components associated with them, can be controlled by rotation of the cam cylinder 70. That is, the cam paths 68, 86 allow translation of the associated followers 66, 84 when the cam paths 68, 86 are substantially parallel to the axis of the auger assembly 10, and substantially prevent motion of the associated followers 66, 84 when the cam paths are substantially perpendicular to the axis of the auger assembly 10. Alternately, only one of the cam followers 66, 84 is used to control the motion of the auger assembly 10 and the cutter 4.

Instead of a cam cylinder 70, a linear cam or a cam having another shape may be used to control the motion of the auger assembly 10 and the cutter 4. Further, in another embodiment, the motion of the auger assembly 10 and the cutter 4 is controlled by one or more different or additional mechanisms. For example, the auger assembly 10 and the cutter 4 may be connected to one or more DC motors or other powered mechanisms, where the motor is controlled by an integrated circuit or other computing device. By controlling the motor, the motion of the auger assembly 10 and the cutter 4 can be controlled.

An assembly 82 is advanced distally as a unit at least partially as far as the first driveshaft 26 advances. The assembly 82 includes the first driveshaft 26, the carriage 58, the seal housing 34, the introducer tube 62, the flexible shaft 24, the auger assembly 10, the cutter 4 and the introducer tip 28. Other components may be included in the assembly 82. Referring also to FIG. 1, a fitting 78 is connected to or formed into the first driveshaft 26 at or near its distal end. The fitting 78 is wider than the first driveshaft 26, and is substantially cylindrical. Alternately, the fitting 78 may be shaped differently. Optionally, the fitting 78 may be beveled or tapered at its distal end. The seal housing 34 may include a beveled or tapered area adjacent to the opening 80 corresponding to any beveling or tapering of the fitting 78. The fitting 78 has a diameter larger than the diameter of the opening 80 in the seal housing 34 through which the flexible shaft 24 extends. Optionally, the fitting 78 may be used to connect or assist in connecting the first driveshaft 26 and the actuator 24. The fitting 78 is positioned on the first driveshaft 26 at a location relative to the opening 80 such that the distal end of the fitting 78 engages the seal housing 34 next to the opening 80 as the first driveshaft 26 is advanced. Thus, the seal housing 34 is impelled forward along with the first driveshaft 26, due to contact between the fitting 78 and the seal housing 34. The initial distance between the fitting 78 and the seal housing 34 is related to the distance along which the assembly 82 is translated. As the seal housing 34 advances, the introducer tip 28 fixed to it is advanced into the opening created by the auger 6 and the cutter 4 in order to maintain hemostasis, as is described in greater detail below.

Alternately, the assembly 82 does not advance as a unit. Instead, the first driveshaft 26 advances the flexible shaft 24 distally, and the auger assembly 10 and cutter 4 advance distally as a result. The introducer tip 28 may be configured to advance into the opening created by the auger 6 and the cutter 4 at a later time, or may be configured to rest on the target vessel before the auger assembly 10 and the cutter 4 advance distally.

The operation of the auger assembly 10 and the cutter 4 of FIGS. 1-3 will now be described. Referring to FIGS. 11-12, a contact structure 110 is connected to or formed into the casing 98, and has an open perimeter. The perimeter of the contact structure 110 may take the shape of a circle with an arc removed, a U-shape, or other shape. The contact structure 110 is placed against the vessel to substantially stabilize its surface within the perimeter of the contact structure 110, such that the tubular vessel is not substantially flattened by the pressure applied to it via the contact structure 110. The cutter 4 and the auger assembly 10 are free to rotate and translate a fixed amount relative to the contact structure 110. Thus, the total translation of the cutter 4 and auger 6 relative to the contact structure 110 is known. The cutter 4 and auger 6 are placed on the vessel at a location where the diameter of the vessel is large enough to ensure that the cutter 4 and auger 6 do not encounter the rear wall of the vessel during their travel relative to the contact structure.

The distal end of the spike 5 of the auger 6 extends distally beyond the distal surface of the contact structure 110. Thus, as the contact structure 110 is moved toward against the vessel, the distal end of the spike 5 penetrates the vessel wall before the contact structure 110 contacts the vessel. The entry into the vessel wall of the spike 5 prior to actuation of the cutter 4 and the auger 6 facilitates tissue removal from the vessel wall. The vessel wall is intact before the spike 5 enters it, and no separate incision need be made in the vessel wall before the spike 5 encounters it.

Energy is applied impulsively to the auger assembly 10 and the cutter 4. The auger assembly 10 and the cutter 4 then begin to rotate, as they advance distally into the vessel wall. Rotation begins at substantially the same time as translation. However, rotation or translation may begin first. The auger 6 advances into the wall of the tubular vessel as the cutter 4 advances and cuts. The cutting action of the cutter 4 is both rotational and axial. By constructing the auger 6 and the cutter 4 to be substantially smooth and radially symmetrical, the rotary motion of these structures creates a substantially smooth and clean hole through the vessel wall. The tissue of the tubular vessel may be strain rate sensitive, such as the tissue of the aorta. Strain rate sensitive tissue is easier to cut when the cutting is performed rapidly than when it is performed slowly. By actuating the auger 6 and the cutter 4 impulsively, they move rapidly such that the cutter 4 can better cut strain rate sensitive tissue.

After the cutter 4 has penetrated the entire vessel wall, it has cut tissue from that vessel wall, and formed an opening corresponding to the former position of that tissue. The cutter 4 cuts a substantially cylindrical tissue plug from the vessel wall due to its tubular shape. The spike 5 is positioned relative to the cutter such that the tissue plug is held within the cutter 4 due to engagement with the ledge 9 after the tissue plug has been cut. That is, the ledge 9 has advanced completely through the vessel wall before the cutter 4, such that the tissue plug cut from the vessel wall is located proximally to the ledge 9 upon its creation. The ledge 9 is wide enough to reliably hold the tissue plug within the cutter 4. The shaft 7 extends axially through the tissue plug, such that contact between the shaft 7 and the tissue plug acts substantially to prevent radial motion of the tissue plug in the cutter 4.

The distal translation of the cutter 4 and auger 6 continues through a fixed distance greater than the thickness of the vessel wall, to ensure that the cutter 4 has completely penetrated the vessel wall. Thus, the cutter 4 and auger 6 may continue to advance for a short distance after the tissue plug has been cut out of the vessel wall having a particular wall thickness. The cutter 4 and auger 6 are then retracted through the introducer tip 28. As they are retracted, they retract the tissue plug, leaving an opening in the vessel wall.

The introducer tip 28 follows the cutter 4 and the auger 6 into the vessel wall, and remains in the opening thus formed, in order to provide hemostasis with regard to that opening. The introducer tip 28 is hollow, and has a diameter slightly larger than the opening. Thus, the introducer tip 28 fits snugly within that opening in order to prevent leakage of fluid from within the vessel between the introducer tip 28 and the opening. Fluid such as blood enters the seal housing 34 through the introducer tip 28, and the seal housing 34 maintains hemostasis with regard to the fluid in the vessel. Alternately, the introducer tip 28 is not used, such that fluid such as blood enters the seal housing 34 through the cutter 4. One or more tools deployed through the introducer tube 62 have an outer diameter slightly smaller than the inner diameter of the introducer tube 62, such that the close fit between the introducer tube 62 and the tools deployed within it substantially provides hemostasis and prevents leakage from the seal housing 34. Alternately, a valve or seal (not shown) may be provided between the introducer tube 62 and the seal housing 34 to substantially prevent blood from entering the lumen of the introducer tube 62. Thus, the seal housing 34 maintains hemostasis in conjunction with the introducer tip 28 and/or the cutter 4. The introducer tip 28 may be omitted where the auger 6 and cutter 4 are part of an independent cutting tool rather than an integrated anastomosis tool or other integrated tool.

The auger assembly 10 and cutter 4 work similarly where the auger 6 is configured as shown in FIGS. 4-5. The contact structure 110 is placed against the vessel wall. The auger 6 and the cutter 4 initially are located proximal to the distal surface of the contact structure 110 and do not contact the vessel wall. As described above, energy is applied impulsively to the auger assembly 10 and the cutter 4, which begin to rotate and also begin to translate toward the wall of a tubular vessel. Thus, the auger assembly 10 and the cutter 4 each have both angular and linear momentum when they encounter the wall of the tubular vessel. The auger 6 encounters the vessel wall before the cutter 4, because the tip of the auger 6 extends distally beyond the distal end of the cutter 4. The vessel wall is intact before the auger 6 encounters it. That is, no separate incision need be made in the wall of the tubular vessel before the auger 6 and cutter 4 encounter it.

Figure 13:
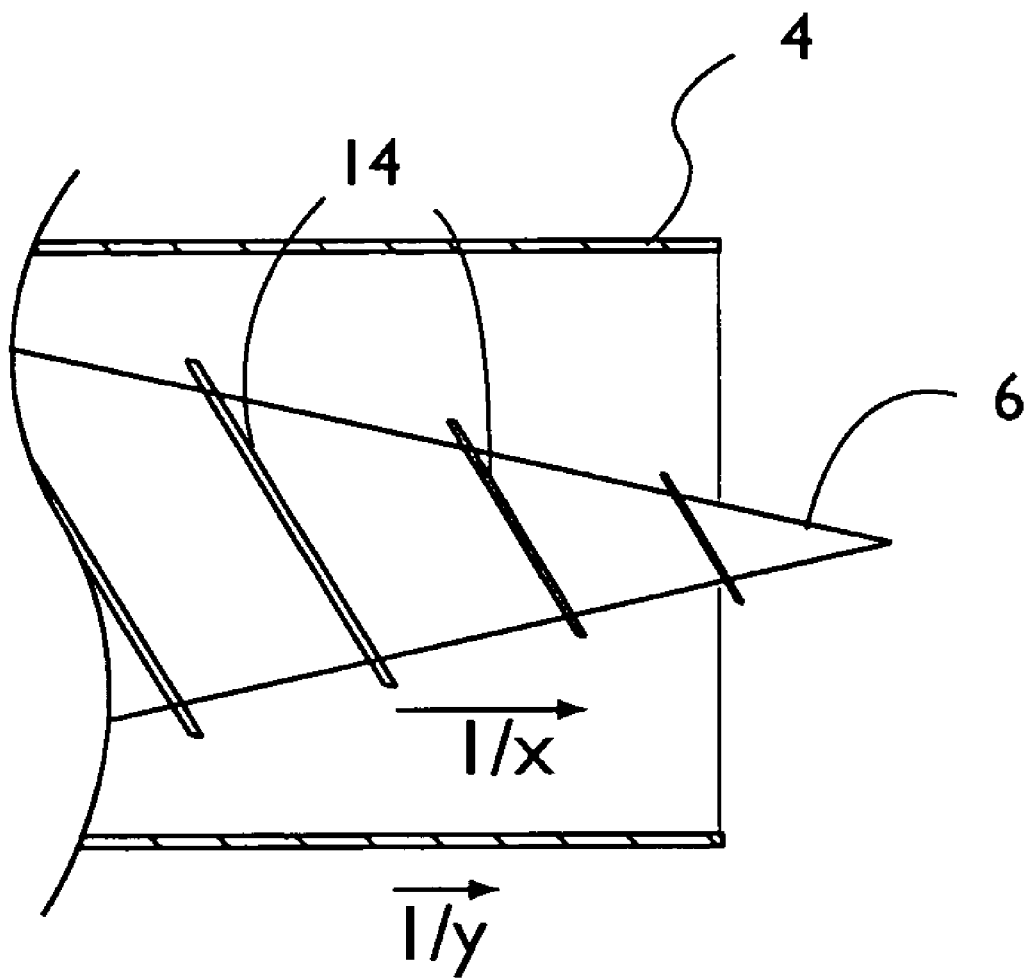
FIG. 13 is a detail view of the auger and cutter of FIGS. 4-5.

Referring also to FIG. 13, half of the cutter 6 is cut away in order to illustrate the auger 6 more completely. The auger flutes 13 have a pitch X, meaning that the flutes 13 cause the auger 6 to penetrate a distance 1/X into the wall of the tubular vessel for each revolution of the auger 6. Thus, at a pitch of 16 threads per inch, the auger 6 advances into the tubular vessel 1/16 inch each revolution of the auger 6. Similarly, the threads of the threaded portion 72 of the first driveshaft 26 have a pitch Y. Thus, at a pitch of 25 threads per inch, the auger 6 and the cutter 4 translate distally 1/25 inch each revolution of the first driveshaft 26. The auger assembly 10 and the first driveshaft 26 are fixed to one another and thus rotate at the same rate. The distance 1/X is greater than the distance 1/Y. Both distances are measured relative to the contact structure 110, which provides a point of reference as to the motion of the auger 6 and the cutter 4. The auger 6 advances into the wall of the tubular vessel faster than the cutter 4, even though the auger 6 and cutter 4 are impelled distally at the same rate. As a result, the auger 6 pulls the wall of the tubular vessel proximally as the cutter 4 advances distally, thereby pulling tissue into the cutter 4. The auger 6 pulls the wall of the tubular vessel intramurally; that is, by engaging the wall across its thickness using the flutes 13, to firmly and reliably engages the wall of the tubular vessel.

The cutter 4 is translated distally through the wall of the tubular vessel as the auger 6 holds a portion of the wall and pulls it proximally relative to the cutter 4. Thus, the cutter 4 cuts the tubular vessel from the outside while the auger 6 holds the wall of the tubular vessel. The auger 6 advances into the wall of the tubular vessel as the cutter 4 advances and cuts. The cutting action of the cutter 4 is both rotational and axial. The tissue of the tubular vessel may be strain rate sensitive, such as the tissue of the aorta. Strain rate sensitive tissue is easier to cut when the cutting is performed rapidly than when it is performed slowly. By actuating the auger 6 and the cutter 4 impulsively, they move rapidly such that the cutter 4 can better cut strain rate sensitive tissue, and enter the tissue quickly enough to minimize any effects of the tissue pulling outward from the opening in directions substantially perpendicular to the motion of the cutter 4. The pitch of the auger flutes 13 and the distance traveled by the cutter 4 during one rotation of the auger 6 are selected such that the auger 6 and cutter 4 cut a substantially cylindrical tissue plug from the wall of the tubular vessel. Alternately, the pitch of the auger flutes 13 and the distance traveled by the cutter 4 during one rotation of the auger 6 are selected such that the auger 6 and cutter 4 cut a substantially conical tissue plug from the wall of the tubular vessel. The conical tissue plug may be wider at its distal end or at its proximal end, depending on the selected pitch of the auger flutes 13 and the distance traveled by the cutter 4 during one rotation of the auger 6.

After the cutter 4 has penetrated the entire vessel wall, it has cut a tissue plug from that wall, and formed an opening corresponding to the former position of that tissue plug. The tissue plug is held firmly in the cutter 4 due to engagement with the auger flutes 13. The distal translation of the cutter 4 and auger 6 continues through a fixed distance greater than the thickness of the vessel wall, to ensure that the cutter 4 has completely penetrated the vessel wall. Thus, the cutter 4 and auger 6 may continue to advance for a short distance after the tissue plug has been cut out of the vessel wall. The cutter 4 and auger 6 are then retracted through the introducer tip 28. As they are retracted, they retract the tissue plug, leaving an opening in the wall of the tubular vessel.

Actuation of the auger 6 and the cutter 4 to remove a tissue plug from a vessel wall and create an opening therein may be performed in a number of different ways. Referring to FIGS. 11-12, in one exemplary embodiment, the cutter 4 and auger 6 are part of an integrated anastomosis tool 100. A single control on the integrated anastomosis tool 100 may be operated by the user to actuate the cutter 4 and the auger 6 and create an opening in the wall of the tubular vessel. This single control may be the knob 88, which is rotated through a preselected number of degrees in order to deploy the cutter 4 and auger 6, cut a tissue plug from the wall of the tubular vessel to form an opening in that wall, and retract the tissue plug out of the opening. A different control than the knob 88 may be provided, such as a lever, a slider, a button, or other control. The single control may be hand-driven, where force transmitted through the operator's hand drives at least part of the operation of the cutter 4 and auger 6, or may be powered, such that the operator simply presses a button or actuates a different control such that a powered mechanism such as a motor drives at least part of the operation of the cutter 4 and auger 6.

Referring to FIG. 11, the integrated anastomosis tool 100 is in the initial state; the auger 6 and the cutter 4 have not yet been deployed and the knob 88 is in an initial position. The user places the contact structure 110 against the wall of the tubular vessel in the location where the opening is to be made, without substantially deforming the tubular vessel. The user then begins to turn the knob 88. The stops 102 on the second driveshaft 52 are biased against the proximal surface 104 of the endplate 94 of the knob 88, as described above. The second driveshaft 52 does not substantially rotate upon rotation of the knob 88, because the registration features 64 connected to the second driveshaft 52 restrain the second driveshaft 52 against rotational movement, as described above. Initially, the slot 96 in the endplate 94 of the knob 88 is not aligned with the stops 102; instead, the stops 102 are in contact with the endplate 94 of the knob 88. At a preselected point in the angular travel of the knob 88, the slot 96 aligns with the stops 102, freeing the stops 102 to translate distally through the slot 102 and allowing the second driveshaft 52 to advance distally under the influence of the compression spring 106. Thus, the rotation of the knob 88 advances the second driveshaft 52 distally at a preselected point in the angular travel of the knob 88.

The distal advancement of the second driveshaft 52 translates the second gear 50 axially relative to the first gear 46. As described above, the first gear 46 is fixed, and engages the second gear 50 both before and after its advancement. As the second driveshaft 52 advances distally, the registration feature or features 64 advance distally relative to the structures or mechanisms that had previously restrained the second driveshaft 52 against rotation, freeing the registration feature or features 64. The second driveshaft 52 is then rotationally free, and begins to rotate driven by the energy stored within the spring 54. This stored energy is impulsively delivered, and in one embodiment causes the second gear 50 to rotate substantially three times. The gear ratio between the first gear 44 and the second gear 50 is chosen to produce the desired number of rotations of the second gear 50 upon release of stored energy from the spring 54. The second gear 50 rotates with the second driveshaft 52, causing the first gear 46 and the first driveshaft 26 to rotate in the opposite direction. Rotation of the first gear 46 also causes the first driveshaft 26 to advance distally, as described above. The actuator 24 transmits the rotary and translational motion of the first driveshaft 26 to the auger assembly 10 and the cutter 4.

The knob 88 is connected to the cam cylinder 70, such that rotation of the knob 88 rotates the cam cylinder 70. When the knob 88 is rotated to the position at which the second driveshaft 52 is allowed to advance distally, the first cam path 68 is positioned relative to the first cam follower 66 on the introducer tube 62 such that the first cam follower 66 and the introducer tube 62 are free to advance distally. The second cam follower 84 extending from the carriage 58 is prevented from moving substantially distally or proximally by the second cam path 86, which at this time is substantially perpendicular to the direction of motion of the introducer tube 62. Because the carriage 58 is held substantially fixed, the rotation of the threaded portion 72 of the first driveshaft 26 relative to the threaded passage 74 in the carriage 58 is converted to distal translation of the first driveshaft 26 as well. As the first driveshaft 26 advances distally, the fitting 78 on the first driveshaft 26 engages the seal housing 34 and impels it forward. The seal housing 34 is connected to the introducer tube 62, and is free to advance distally along with the introducer tube 62. Thus, the seal housing 34 and the components fixed to it, such as the introducer tip 28, advance distally. The integrated anastomosis tool 100 is then in the deployed state of FIG. 12.

Where the auger 6 is fluted, as is FIGS. 4-5, the cam cylinder 70 controls the motion of the auger 6 and cutter 4 in the same manner as described above. The portions of the cam paths 68, 86 allowing for translation are longer than described above, because the auger 6 and the cutter 4 are initially spaced apart from the vessel wall, and thus travel a further distance during their actuation. The auger 6 and the cutter 4 penetrate the intact vessel wall, cut a tissue plug to form an opening, and retract the tissue plug from the opening in the same manner as described above.

The user continues to rotate the knob 88. After the tissue plug has been cut from the wall of the tubular vessel, it is restrained within the cutter 4 as described above. The auger 6 and cutter 4 continue advancing until they have traveled the entire preselected distance extending distally from the contact structure 110. The auger 6 and the cutter 4 then are retracted. The second cam follower 84 travels within the second cam path 86 in the cam cylinder 70. As the cam cylinder 70 rotates as the knob 88 is turned, the second cam path 86 moves proximally relative to the second cam follower 84. That is, the second cam path 86 has an axial component, such that contact between the second cam path 86 and the second cam follower 84 translates the second cam follower 84 proximally. Because the second cam follower 84 is connected to the carriage 58, the carriage 58 also is moved proximally, such that the auger 6 and the cutter 4, as well as the tissue plug they restrain, are removed from the opening in the wall of the tubular vessel through the introducer tip 28, which remains in the opening. The bushing 38 is retracted along with the auger assembly 10. Thus, an assembly that includes the cutter 4, the auger assembly 10 and the bushing 38 is retracted from the opening in the wall of the tubular vessel. The orientation of the auger 6 before this retraction defines a first axis.

As the bushing 38 moves proximally, the guide follower or followers on the bushing 38 are guided by the guides 35 within the seal housing 34. The guides 35 extend away from the first axis in order to move the bushing 38 away from the first axis as the bushing is moved proximally. That is, the auger 6 and the cutter 4 are moved off-axis during retraction. In one embodiment, moving proximally, each guide 35 slopes in a direction toward the opening 80. Thus, as the bushing 38 is retracted proximally, the guide followers encounter the upward-sloping guides 35, which cause the bushing 38 to move off the first axis to a second axis. The guide followers need not contact the guides 35 at all points during the retraction of the bushing. Indeed, the actuator 24 itself may be configured to bias the bushing 38, auger assembly 10 and cutter 4 away from the first axis. In this way, the auger 6, cutter 4 and the tissue plug that they retain, as well as the bushing 38, are moved off the first axis such that an anastomosis device can be deployed along the first axis through the introducer tube 62. Further, moving the auger 6 and cutter 4 off the first axis allows the tissue plug to be removed from the opening without being retracted through the graft vessel. By moving the tissue plug into a location within the seal housing 34, hemostasis is maintained.

Alternately, the guides 35 and guide followers need not be provided. For example, the guides 35 and guide followers may be unnecessary where the auger 6 and cutter 4 are not part of an integrated tool. As another example, the bushing 38, auger assembly 10 and cutter 4 may be retracted substantially along the first axis, and an anastomosis device is moved from another axis to the first axis for deployment. In such an example, the bushing 38 need not be moved off the first axis, and the guides 35 and guide followers are not required.

While the invention has been described in detail, it will be apparent to one skilled in the art that various changes and modifications can be made and equivalents employed, without departing from the present invention. For example, a different mechanism or mechanisms may be used to drive the rotary and translational motion of the auger assembly 10 and the cutter 4. Although embodiments have been described above with regard to a CABG procedure, the apparatus and method described above are not limited to use in such a procedure. Further, the cutter and auger disclosed above may be utilized to create openings in tubular vessels and bodily structures other than blood vessels. It is to be understood that the invention is not limited to the details of construction and/or the arrangements of components set forth in the above description or illustrated in the drawings. Therefore, the invention is not to be restricted or limited except in accordance with the following claims and their legal equivalents.

What is claimed is:

1. A tool for making an incision in and removing tissue from a vessel wall, comprising:
   a cutter; and
   a piercing member positioned within said cutter, wherein said piercing member and said cutter are configured to translate together to penetrate the wall of the vessel.

2. The tool of claim 1, wherein said piercing member is configured to allow rotation relative to said cutter.

3. The tool of claim 1, wherein said piercing member is rotationally fixed to said cutter.

4. The tool of claim 1, wherein said cutter is a curved blade having a substantially circular distal end.

5. The tool of claim 1, wherein said cutter is a curved blade having an open perimeter at its distal end.

6. The tool of claim 1, wherein the distal end of said cutter is beveled inward.

7. The tool of claim 1, wherein the distal end of said cutter is beveled outward.

8. The tool of claim 1, wherein the distal tip of said piercing member extends further in the distal direction than the distal end of said cutter.

9. The tool of claim 1, wherein said piercing member holds the tissue removed from the wall of the vessel.

10. The tool of claim 1, wherein said cutter is substantially hemostatic.

11. The tool of claim 1, wherein said piercing member is an auger.

12. The tool of claim 11, wherein said auger and said cutter are substantially coaxial.

13. The tool of claim 11, wherein said auger comprises:
a spike;
a shaft connected to and extending distally from said spike, said shaft fixed to said cutter.

14. The tool of claim 13, wherein said spike is substantially conical at its distal end.

15. The tool of claim 14, wherein the width of the proximal end of said spike is greater than the width of said shaft.

16. The tool of claim 11, wherein at least one flute is defined in said auger.

17. A surgical tool for removing tissue from the wall of a vessel to create an opening, comprising:
a rotatable cutter;
an auger assembly fixed to and substantially coaxial with said cutter, said auger assembly comprising an auger at its distal end;
an actuator connected to at least one of said auger assembly and said cutter.

18. The surgical tool of claim 17, wherein said actuator is a flexible shaft.

19. The surgical tool of claim 17, wherein said actuator is a coil spring.

20. The surgical tool of claim 17, wherein said actuator is retractable.

21. The surgical tool of claim 17, wherein said actuator extends away from the axis of said cutter.

22. The surgical tool of claim 17, wherein said cutter is vented.

23. The surgical tool of claim 22, wherein said auger further comprises at least one centering flange between and connected to said auger and said cutter, wherein each said centering flange comprises a slot extending therethrough.

24. The surgical tool of claim 23, wherein at least one centering flange comprises a substantially circumferential groove defined therein.

25. The surgical tool of claim 17, further comprising a casing, said casing comprising a contact structure at its distal end, wherein said auger and said cutter translate relative to said contact structure.

26. The surgical tool of claim 25, wherein said contact structure has an open perimeter.

27. The surgical tool of claim 25, wherein said auger and said cutter translate distally a selected amount relative to said contact structure.

28. The surgical tool of claim 17, further comprising a knob operatively connected to said coil spring.

29. The surgical tool of claim 28, wherein said knob is rotatable through two or more positions, and wherein actuation of said auger and said cutter is controlled by rotation of said knob.

30. The surgical tool of claim 17, further comprising
a seal housing; and
an introducer tip connected to said seal housing, wherein said auger and said cutter are configured to slide through said introducer tip.

31. The surgical tool of claim 30, wherein said auger and said cutter are configured for withdrawal into said seal housing.

32. The surgical tool of claim 30, wherein said introducer tip is expandable.

33. The surgical tool of claim 30, wherein said seal housing comprises at least one guide.

34. The surgical tool of claim 33, further comprising a bushing connected to said coil spring, said bushing comprising at least one guide follower configured to engage said guide.

35. The surgical tool of claim 33, wherein said introducer defines a first axis, and wherein said guide extends away from said first axis.

36. The surgical tool of claim 33, wherein said introducer defines a first axis, and wherein said coil spring is moveable in a direction at an angle to said first axis.

37. The surgical tool of claim 17, wherein the distal end of said auger extends distally beyond the distal end of said cutter.

38. The surgical tool of claim 17, further comprising an impulse source configured to rotate and translate said auger and said cutter.

39. The surgical tool of claim 38, wherein said impulse source is a spring.

40. The surgical tool of claim 38, further comprising:
a rotatable first driveshaft connected to said coil spring; and
a axially fixed first gear comprising an opening through which said first driveshaft extends, wherein said first driveshaft is slidable relative to said first gear, and wherein rotation of said first gear causes said first driveshaft to rotate.

41. The surgical tool of claim 40, wherein said first driveshaft comprises at least one rib aligned extending substantially radially outward and said first gear comprises a passage therethrough configured to engage said at least one rib.

42. The surgical tool of claim 41, wherein said at least one rib extends substantially axially along said first driveshaft.

43. The surgical tool of claim 40, further comprising a carriage having a threaded passage therein, said first driveshaft further comprising a threaded portion configured to engage said threaded passage, wherein rotary motion of said first driveshaft causes said first driveshaft to translate distally relative to said carriage.

44. The surgical tool of claim 43, further comprising:
a second driveshaft; and
a second gear connected to said second driveshaft, said second gear configured to engage said first gear, wherein rotation of said second gear causes said first gear to rotate.

45. The surgical tool of claim 44, further comprising at least one registration member extending from at least one of the second driveshaft and the second gear.

46. The surgical tool of claim 45, wherein at least one said registration member is configured to restrain said second driveshaft against rotational motion and allow translational motion.

47. The surgical tool of claim 44, further comprising:
a cam cylinder operationally connected to said auger and said cutter, said cam cylinder comprising at least one cam path defined therein; and
a knob connected to said cam cylinder.

48. The surgical tool of claim 47, wherein said auger and said cutter are actuated based on the position of said knob.

49. The surgical tool of claim 47, further comprising:
an introducer tube;
a first cam follower connected to said introducer tube; and
a second cam follower connected to said carriage;
wherein each said cam follower rides within one said cam path.

50. The surgical tool of claim 49, wherein rotation of said cam cylinder causes said at least one cam path to move relative to and cause translation of at least one said cam follower.

51. The surgical tool of claim 38, wherein said impulse source imparts angular and linear momentum to said auger and said cutter before said auger and said cutter contact the wall of the vessel.

* * * * *